(12) United States Patent
Vidlund et al.

(10) Patent No.: US 7,247,134 B2
(45) Date of Patent: Jul. 24, 2007

(54) DEVICES AND METHODS FOR HEART VALVE TREATMENT

(75) Inventors: Robert M. Vidlund, Maplewood, MN (US); Craig Ekvall, Elk River, MN (US); David Kusz, Minneapolis, MN (US); Cyril J. Schweich, Jr., Maple Grove, MN (US)

(73) Assignee: Myocor, Inc., Maple Grove, MN (US)

( * ) Notice: Subject to any disclaimer, the term of this patent is extended or adjusted under 35 U.S.C. 154(b) by 144 days.

(21) Appl. No.: 10/704,145

(22) Filed: Nov. 10, 2003

(65) Prior Publication Data

US 2004/0148020 A1 Jul. 29, 2004

Related U.S. Application Data

(60) Provisional application No. 60/425,519, filed on Nov. 12, 2002.

(51) Int. Cl.
*A61M 31/00* (2006.01)
*A61F 2/36* (2006.01)

(52) U.S. Cl. ......................................... 600/16; 623/2.1

(58) Field of Classification Search ...... 623/2.36–2.38, 623/3.1, 94; 606/108; 600/16, 13
See application file for complete search history.

(56) References Cited

U.S. PATENT DOCUMENTS

| | | | |
|---|---|---|---|
| 963,899 | A | 7/1910 | Kistler |
| 3,019,790 | A | 2/1962 | Militana |
| 3,656,185 | A | 4/1972 | Carpenter |
| 3,980,086 | A | 9/1976 | Kletschka et al. |
| 4,035,849 | A | 7/1977 | Angell et al. |
| 4,055,861 | A | 11/1977 | Carpentier et al. |
| 4,192,293 | A | 3/1980 | Asrican |
| 4,217,665 | A | 8/1980 | Bex et al. |
| 4,261,342 | A | 4/1981 | Aranguren Duo |
| 4,300,564 | A | 11/1981 | Furihata |
| 4,306,319 | A | 12/1981 | Kaster |

(Continued)

FOREIGN PATENT DOCUMENTS

DE 36 14 292 C1 11/1987

(Continued)

OTHER PUBLICATIONS

Edie, M.D. et al., "Surgical repair of single ventricle, "*The Journal of Thoracic and Cardiovascular Surgery*, vol. 66, No. 3, Sep. 1973, pp. 350-360.

(Continued)

*Primary Examiner*—Suzette Gherbi
(74) *Attorney, Agent, or Firm*—Finnegan, Henderson, Farabow, Garrett & Dunner, LLP

(57) ABSTRACT

Devices and methods for improving the function of a valve (e.g., mitral valve) by positioning an implantable device outside and adjacent the heart wall such that the device alters the shape of the heart wall acting on the valve. The implantable device may alter the shape of the heart wall acting on the valve by applying an inward force and/or by circumferential shortening (cinching). The shape change of the heart wall acting on the valve is sufficient to change the function of the valve, and may increase coaptation of the leaflets, for example, to reduce regurgitation.

22 Claims, 18 Drawing Sheets

U.S. PATENT DOCUMENTS

| | | | |
|---|---|---|---|
| 4,343,048 A | 8/1982 | Ross et al. | |
| 4,372,293 A | 2/1983 | Vijil-Rosales | |
| 4,409,974 A | 10/1983 | Freedland | |
| 4,536,893 A | 8/1985 | Parravicini | |
| 4,579,120 A | 4/1986 | MacGregor | |
| 4,592,342 A | 6/1986 | Salmasian | |
| 4,629,459 A | 12/1986 | Ionescu et al. | |
| 4,690,134 A | 9/1987 | Snyders | |
| 4,705,040 A | 11/1987 | Mueller et al. | |
| 4,936,857 A | 6/1990 | Kulik | |
| 4,944,753 A | 7/1990 | Burgess et al. | |
| 4,960,424 A | 10/1990 | Grooters | |
| 4,997,431 A | 3/1991 | Isner et al. | |
| 5,061,277 A | 10/1991 | Carpentier et al. | |
| 5,104,407 A | 4/1992 | Lam et al. | |
| 5,106,386 A | 4/1992 | Isner et al. | |
| 5,131,905 A | 7/1992 | Grooters | |
| RE34,021 E | 8/1992 | Mueller et al. | |
| 5,156,621 A | 10/1992 | Navia et al. | |
| 5,169,381 A | 12/1992 | Snyders | |
| 5,192,314 A | 3/1993 | Daskalakis | |
| 5,250,049 A | 10/1993 | Michael | |
| 5,258,015 A | 11/1993 | Li et al. | |
| 5,284,488 A | 2/1994 | Sideris | |
| 5,300,087 A | 4/1994 | Knoepfler | |
| 5,312,642 A | 5/1994 | Chesterfield et al. | |
| 5,360,444 A | 11/1994 | Kusuhara | |
| 5,376,112 A | 12/1994 | Duran | |
| 5,385,528 A | 1/1995 | Wilk | |
| 5,389,096 A | 2/1995 | Aita et al. | |
| 5,417,709 A | 5/1995 | Slater | |
| 5,433,727 A | 7/1995 | Sideris | |
| 5,445,600 A | 8/1995 | Abdulla | |
| 5,450,860 A | 9/1995 | O'Connor | |
| 5,452,733 A | 9/1995 | Sterman et al. | |
| 5,458,574 A | 10/1995 | Machold et al. | |
| 5,496,305 A | 3/1996 | Kittrell et al. | |
| 5,509,428 A | 4/1996 | Dunlop | |
| 5,522,884 A | 6/1996 | Wright | |
| 5,533,958 A | 7/1996 | Wilk | |
| 5,571,215 A | 11/1996 | Sterman et al. | |
| 5,584,803 A | 12/1996 | Stevens et al. | |
| 5,593,424 A * | 1/1997 | Northrup, III | 606/232 |
| 5,607,471 A | 3/1997 | Seguin et al. | |
| 5,665,092 A | 9/1997 | Mangiardi et al. | |
| 5,674,279 A | 10/1997 | Wright et al. | |
| 5,682,906 A | 11/1997 | Sterman et al. | |
| 5,702,343 A | 12/1997 | Alferness | |
| 5,713,954 A | 2/1998 | Rosenberg et al. | |
| 5,718,725 A | 2/1998 | Sterman et al. | |
| 5,755,783 A | 5/1998 | Stobie et al. | |
| 5,758,663 A | 6/1998 | Wilk et al. | |
| 5,766,234 A | 6/1998 | Chen et al. | |
| 5,776,189 A | 7/1998 | Khalid et al. | |
| 5,800,334 A | 9/1998 | Wilk | |
| 5,800,528 A | 9/1998 | Lederman et al. | |
| 5,800,531 A | 9/1998 | Cosgrove et al. | |
| 5,807,384 A | 9/1998 | Mueller | |
| 5,814,097 A | 9/1998 | Sterman et al. | |
| 5,824,066 A | 10/1998 | Gross | |
| 5,824,069 A | 10/1998 | Lemole | |
| 5,840,059 A | 11/1998 | March et al. | |
| 5,849,005 A | 12/1998 | Garrison et al. | |
| 5,855,601 A | 1/1999 | Bessler et al. | |
| 5,855,614 A | 1/1999 | Stevens et al. | |
| 5,865,791 A | 2/1999 | Whayne et al. | |
| 5,876,436 A | 3/1999 | Vanney et al. | |
| 5,888,240 A | 3/1999 | Carpentier et al. | |
| 5,902,229 A | 5/1999 | Tsitlik et al. | |
| 5,928,281 A | 7/1999 | Huynh et al. | |
| 5,944,738 A | 8/1999 | Amplatz et al. | |
| 5,957,977 A | 9/1999 | Melvin | |
| 5,961,440 A | 10/1999 | Schweich, Jr. et al. | |
| 5,961,539 A | 10/1999 | Northrup, III et al. | |
| 5,961,549 A | 10/1999 | Nguyen et al. | |
| 5,967,990 A | 10/1999 | Thierman et al. | |
| 5,971,910 A | 10/1999 | Tsitlik et al. | |
| 5,971,911 A | 10/1999 | Wilk | |
| 5,972,022 A | 10/1999 | Huxel | |
| 5,972,030 A | 10/1999 | Garrison et al. | |
| 5,984,857 A | 11/1999 | Buck et al. | |
| 5,984,917 A | 11/1999 | Fleischman et al. | |
| 5,999,678 A | 12/1999 | Murphy-Chutorian et al. | |
| 6,001,126 A | 12/1999 | Nguyen-Thien-Nhon | |
| 6,019,722 A | 2/2000 | Spence et al. | |
| 6,024,096 A | 2/2000 | Buckberg | |
| 6,024,756 A | 2/2000 | Huebsch et al. | |
| 6,045,497 A | 4/2000 | Schweich, Jr. et al. | |
| 6,050,936 A | 4/2000 | Schweich, Jr. et al. | |
| 6,059,715 A | 5/2000 | Schweich, Jr. et al. | |
| 6,071,303 A | 6/2000 | Laufer | |
| 6,077,214 A * | 6/2000 | Mortier et al. | 600/16 |
| 6,077,218 A | 6/2000 | Alferness | |
| 6,079,414 A | 6/2000 | Roth | |
| 6,085,754 A | 7/2000 | Alferness et al. | |
| 6,086,532 A | 7/2000 | Panescu et al. | |
| 6,095,968 A | 8/2000 | Snyders | |
| 6,102,944 A | 8/2000 | Huynh et al. | |
| 6,110,100 A | 8/2000 | Talpade | |
| 6,113,536 A | 9/2000 | Aboul-Hosn et al. | |
| 6,117,159 A | 9/2000 | Huebsch et al. | |
| 6,120,520 A | 9/2000 | Saadat et al. | |
| 6,123,662 A | 9/2000 | Alferness et al. | |
| 6,125,852 A | 10/2000 | Stevens et al. | |
| 6,126,590 A | 10/2000 | Alferness | |
| 6,129,758 A | 10/2000 | Love | |
| 6,132,438 A | 10/2000 | Fleischman et al. | |
| 6,143,025 A | 11/2000 | Stobie et al. | |
| 6,155,968 A | 12/2000 | Wilk | |
| 6,155,972 A | 12/2000 | Nauertz et al. | |
| 6,162,168 A * | 12/2000 | Schweich et al. | 600/16 |
| 6,165,119 A | 12/2000 | Schweich, Jr. et al. | |
| 6,165,120 A | 12/2000 | Schweich, Jr. et al. | |
| 6,165,121 A | 12/2000 | Alferness | |
| 6,165,122 A | 12/2000 | Alferness | |
| 6,165,183 A | 12/2000 | Kuehn et al. | |
| 6,169,922 B1 | 1/2001 | Alferness et al. | |
| 6,174,279 B1 | 1/2001 | Girard | |
| 6,174,332 B1 | 1/2001 | Loch et al. | |
| 6,179,791 B1 | 1/2001 | Krueger | |
| 6,182,664 B1 | 2/2001 | Cosgrove | |
| 6,183,411 B1 | 2/2001 | Mortier et al. | |
| 6,183,512 B1 * | 2/2001 | Howanec et al. | 623/2.36 |
| 6,190,408 B1 * | 2/2001 | Melvin | 623/3.1 |
| 6,193,648 B1 | 2/2001 | Krueger | |
| 6,197,053 B1 | 3/2001 | Cosgrove et al. | |
| 6,206,004 B1 | 3/2001 | Schmidt et al. | |
| 6,206,820 B1 | 3/2001 | Kazi et al. | |
| 6,210,432 B1 | 4/2001 | Solem et al. | |
| 6,217,610 B1 | 4/2001 | Carpentier et al. | |
| 6,221,013 B1 | 4/2001 | Panescu et al. | |
| 6,221,103 B1 | 4/2001 | Melvin | |
| 6,221,104 B1 | 4/2001 | Buckberg et al. | |
| 6,224,540 B1 | 5/2001 | Lederman et al. | |
| 6,230,714 B1 | 5/2001 | Alferness et al. | |
| 6,231,561 B1 | 5/2001 | Frazier et al. | |
| 6,231,602 B1 | 5/2001 | Carpentier et al. | |
| 6,238,334 B1 | 5/2001 | Easterbrook, III et al. | |
| 6,241,654 B1 | 6/2001 | Alferness | |
| 6,245,102 B1 | 6/2001 | Jayaraman | |
| 6,245,105 B1 | 6/2001 | Nguyen et al. | |
| 6,250,308 B1 | 6/2001 | Cox | |
| 6,251,061 B1 | 6/2001 | Hastings et al. | |
| 6,258,021 B1 | 7/2001 | Wilk | |

| Patent | Date | Inventor |
|---|---|---|
| 6,258,023 B1 | 7/2001 | Rogers et al. |
| 6,260,552 B1 | 7/2001 | Mortier et al. |
| 6,260,820 B1 | 7/2001 | Chowdhury |
| 6,261,222 B1 | 7/2001 | Schweich, Jr. et al. |
| 6,264,602 B1 | 7/2001 | Mortier et al. |
| 6,269,819 B1 | 8/2001 | Oz et al. |
| 6,283,993 B1 | 9/2001 | Cosgrove et al. |
| 6,290,674 B1 | 9/2001 | Roue et al. |
| 6,293,906 B1 | 9/2001 | Vanden Hoek et al. |
| 6,309,370 B1 | 10/2001 | Haim et al. |
| 6,312,447 B1 | 11/2001 | Grimes |
| 6,314,322 B1 | 11/2001 | Rosenberg |
| 6,328,727 B1 | 12/2001 | Frazier et al. |
| 6,331,157 B2 | 12/2001 | Hancock |
| 6,332,863 B1 | 12/2001 | Schweich, Jr. et al. |
| 6,332,864 B1 | 12/2001 | Schweich, Jr. et al. |
| 6,332,893 B1 | 12/2001 | Mortier et al. |
| 6,338,712 B2 | 1/2002 | Spence et al. |
| 6,343,605 B1 | 2/2002 | Lafontaine |
| 6,360,749 B1 | 3/2002 | Jayaraman |
| 6,370,429 B1 | 4/2002 | Alferness et al. |
| 6,375,608 B1 | 4/2002 | Alferness |
| 6,379,366 B1 | 4/2002 | Fleischman et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,406,422 B1 | 6/2002 | Landesberg |
| 6,409,759 B1 | 6/2002 | Peredo |
| 6,409,760 B1 | 6/2002 | Melvin |
| 6,416,459 B1 | 7/2002 | Haindl |
| 6,419,669 B1 | 7/2002 | Frazier et al. |
| 6,425,856 B1 | 7/2002 | Shapland et al. |
| 6,432,039 B1 | 8/2002 | Wardle |
| 6,432,059 B2 | 8/2002 | Hickey |
| 6,436,088 B2 | 8/2002 | Frazier et al. |
| 6,439,237 B1 | 8/2002 | Buckberg et al. |
| 6,443,949 B2 | 9/2002 | Altman |
| 6,450,171 B1 | 9/2002 | Buckberg et al. |
| 6,458,100 B2 | 10/2002 | Roue et al. |
| 6,461,366 B1 | 10/2002 | Seguin |
| 6,478,729 B1 | 11/2002 | Rogers et al. |
| 6,482,146 B1 | 11/2002 | Alferness et al. |
| 6,494,825 B1 | 12/2002 | Talpade |
| 6,508,756 B1 | 1/2003 | Kung et al. |
| 6,511,426 B1 | 1/2003 | Hossack et al. |
| 6,514,194 B2 | 2/2003 | Schweich, Jr. et al. |
| 6,520,904 B1 | 2/2003 | Melvin |
| 6,537,198 B1 | 3/2003 | Vidlund et al. |
| 6,537,203 B1 | 3/2003 | Alferness et al. |
| 6,537,314 B2 | 3/2003 | Langberg et al. |
| 6,544,167 B2 | 4/2003 | Buckberg et al. |
| 6,544,180 B1 | 4/2003 | Doten et al. |
| 6,547,821 B1 | 4/2003 | Taylor et al. |
| 6,569,198 B1 * | 5/2003 | Wilson et al. ............ 623/2.37 |
| 6,572,529 B2 | 6/2003 | Wilk |
| 6,582,355 B2 | 6/2003 | Alferness et al. |
| 6,587,734 B2 | 7/2003 | Okuzumi |
| 6,589,160 B2 | 7/2003 | Schweich, Jr. et al. |
| 6,592,619 B2 | 7/2003 | Melvin |
| 6,595,912 B2 | 7/2003 | Lau et al. |
| 6,602,182 B1 | 8/2003 | Milbocker |
| 6,602,184 B2 | 8/2003 | Lau et al. |
| 6,612,278 B2 | 9/2003 | Kampichler |
| 6,612,978 B2 | 9/2003 | Lau et al. |
| 6,612,979 B2 | 9/2003 | Lau et al. |
| 6,616,596 B1 | 9/2003 | Milbocker |
| 6,616,684 B1 | 9/2003 | Vidlund et al. |
| 6,619,291 B2 | 9/2003 | Hlavka |
| 6,622,730 B2 | 9/2003 | Ekvail et al. |
| 6,626,821 B1 | 9/2003 | Kung et al. |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,645,139 B2 | 11/2003 | Haindl |
| 6,651,671 B1 | 11/2003 | Donlon et al. |
| 6,656,221 B2 | 12/2003 | Taylor et al. |
| 6,663,558 B2 | 12/2003 | Lau et al. |
| 6,673,009 B1 | 1/2004 | Vanden Hoek et al. |
| 6,676,702 B2 | 1/2004 | Mathis |
| 6,681,773 B2 | 1/2004 | Murphy et al. |
| 6,682,474 B2 | 1/2004 | Lau et al. |
| 6,682,475 B2 | 1/2004 | Cox et al. |
| 6,682,476 B2 | 1/2004 | Alferness et al. |
| 6,685,620 B2 | 2/2004 | Gifford, III et al. |
| 6,685,627 B2 | 2/2004 | Jayaraman |
| 6,685,646 B2 | 2/2004 | Cespedes et al. |
| 6,689,048 B2 | 2/2004 | Vanden Hoek et al. |
| 6,695,768 B1 | 2/2004 | Levine et al. |
| 6,695,866 B1 | 2/2004 | Kuehn et al. |
| 6,701,929 B2 | 3/2004 | Hussein |
| 6,702,732 B1 | 3/2004 | Lau et al. |
| 6,702,763 B2 | 3/2004 | Murphy et al. |
| 6,702,826 B2 | 3/2004 | Liddicoat et al. |
| 6,706,065 B2 | 3/2004 | Langberg et al. |
| 6,709,456 B2 | 3/2004 | Langberg et al. |
| 6,712,804 B2 | 3/2004 | Roue et al. |
| 6,716,158 B2 | 4/2004 | Raman et al. |
| 6,719,767 B1 | 4/2004 | Kimblad |
| 6,723,038 B1 * | 4/2004 | Schroeder et al. ............ 600/16 |
| 6,726,716 B2 | 4/2004 | Marquez |
| 6,726,717 B2 | 4/2004 | Alfieri et al. |
| 6,730,016 B1 | 5/2004 | Cox et al. |
| 6,733,525 B2 | 5/2004 | Yang et al. |
| 6,740,107 B2 | 5/2004 | Loeb et al. |
| 6,752,813 B2 | 6/2004 | Goldfarb et al. |
| 6,755,777 B2 | 6/2004 | Schweich, Jr. et al. |
| 6,755,779 B2 | 6/2004 | Vanden Hoek et al. |
| 6,767,362 B2 | 7/2004 | Schreck |
| 6,769,434 B2 | 8/2004 | Liddicoat et al. |
| 6,776,754 B1 | 8/2004 | Wilk |
| 6,790,231 B2 | 9/2004 | Liddicoat et al. |
| 6,793,673 B2 | 9/2004 | Kowalsky et al. |
| 6,797,001 B2 * | 9/2004 | Mathis et al. ............ 623/2.37 |
| 6,800,090 B2 | 10/2004 | Alferness et al. |
| 6,805,710 B2 | 10/2004 | Bolling et al. |
| 6,810,882 B2 | 11/2004 | Langberg et al. |
| 6,814,700 B1 | 11/2004 | Mueller et al. |
| 6,824,562 B2 | 11/2004 | Mathis et al. |
| 6,830,585 B1 | 12/2004 | Artof et al. |
| 6,837,247 B2 | 1/2005 | Buckberg et al. |
| 6,846,296 B1 | 1/2005 | Milbocker et al. |
| 6,858,039 B2 | 2/2005 | McCarthy |
| 6,875,224 B2 | 4/2005 | Grimes |
| 6,876,887 B2 | 4/2005 | Okuzumi |
| 6,881,185 B2 | 4/2005 | Vanden Hock et al. |
| 6,887,192 B1 | 5/2005 | Whayne et al. |
| 6,890,353 B2 | 5/2005 | Cohn et al. |
| 6,893,392 B2 | 5/2005 | Alferness |
| 6,896,652 B2 | 5/2005 | Alferness et al. |
| 6,902,522 B1 | 6/2005 | Walsh et al. |
| 6,908,426 B2 | 6/2005 | Shapland et al. |
| 6,908,478 B2 * | 6/2005 | Alferness et al. ........ 623/1.11 |
| 6,913,608 B2 | 7/2005 | Liddicoat et al. |
| 6,918,917 B1 | 7/2005 | Nguyen et al. |
| 6,921,407 B2 | 7/2005 | Nguyen et al. |
| 6,949,122 B2 | 9/2005 | Adams et al. |
| 6,951,534 B2 | 10/2005 | Girard et al. |
| 6,955,689 B2 | 10/2005 | Ryan et al. |
| 6,959,711 B2 | 11/2005 | Murphy et al. |
| 6,960,229 B2 | 11/2005 | Mathis et al. |
| 6,962,605 B2 | 11/2005 | Cosgrove et al. |
| 6,966,926 B2 | 11/2005 | Mathis |
| 6,976,995 B2 | 12/2005 | Mathis et al. |
| 2001/0003986 A1 | 6/2001 | Cosgrove |
| 2001/0005787 A1 | 6/2001 | Oz et al. |

| Publication No. | Date | Inventor |
|---|---|---|
| 2001/0009976 A1 | 7/2001 | Panescu et al. |
| 2001/0014800 A1 | 8/2001 | Frazier et al. |
| 2001/0014811 A1 | 8/2001 | Hussein |
| 2001/0018611 A1* | 8/2001 | Solem et al. .............. 623/2.37 |
| 2001/0021874 A1 | 9/2001 | Carpentier et al. |
| 2001/0029314 A1 | 10/2001 | Alferness et al. |
| 2001/0034551 A1 | 10/2001 | Cox |
| 2001/0037123 A1 | 11/2001 | Hancock |
| 2001/0039434 A1 | 11/2001 | Frazier et al. |
| 2001/0039435 A1 | 11/2001 | Roue et al. |
| 2001/0039436 A1 | 11/2001 | Frazier et al. |
| 2001/0041821 A1 | 11/2001 | Wilk |
| 2001/0041914 A1 | 11/2001 | Frazier et al. |
| 2001/0041915 A1 | 11/2001 | Roue et al. |
| 2001/0044568 A1 | 11/2001 | Langberg et al. |
| 2001/0047122 A1 | 11/2001 | Vanden Hoek et al. |
| 2001/0049492 A1 | 12/2001 | Frazier et al. |
| 2002/0007216 A1* | 1/2002 | Melvin ...................... 623/3.11 |
| 2002/0013571 A1 | 1/2002 | Goldfarb et al. |
| 2002/0016628 A1 | 2/2002 | Langberg et al. |
| 2002/0019580 A1 | 2/2002 | Lau et al. |
| 2002/0022880 A1 | 2/2002 | Melvin |
| 2002/0026092 A1 | 2/2002 | Buckberg et al. |
| 2002/0028981 A1 | 3/2002 | Lau et al. |
| 2002/0029783 A1 | 3/2002 | Stevens et al. |
| 2002/0032364 A1 | 3/2002 | Lau et al. |
| 2002/0042554 A1 | 4/2002 | Alferness et al. |
| 2002/0045798 A1 | 4/2002 | Lau et al. |
| 2002/0045799 A1 | 4/2002 | Lau et al. |
| 2002/0045800 A1 | 4/2002 | Lau et al. |
| 2002/0052538 A1 | 5/2002 | Lau et al. |
| 2002/0056461 A1 | 5/2002 | Jayaraman |
| 2002/0058855 A1 | 5/2002 | Schweich, Jr. et al. |
| 2002/0065449 A1 | 5/2002 | Wardle |
| 2002/0065465 A1 | 5/2002 | Panescu et al. |
| 2002/0065554 A1 | 5/2002 | Streeter |
| 2002/0068850 A1 | 6/2002 | Vanden Hoek et al. |
| 2002/0077532 A1 | 6/2002 | Gannoe et al. |
| 2002/0082647 A1 | 6/2002 | Alferness et al. |
| 2002/0087173 A1 | 7/2002 | Alferness et al. |
| 2002/0091296 A1 | 7/2002 | Alferness |
| 2002/0103511 A1 | 8/2002 | Alferness et al. |
| 2002/0103532 A1 | 8/2002 | Langberg et al. |
| 2002/0103533 A1 | 8/2002 | Langberg et al. |
| 2002/0111533 A1 | 8/2002 | Melvin |
| 2002/0111567 A1 | 8/2002 | Vanden Hoek et al. |
| 2002/0111636 A1 | 8/2002 | Fleischman et al. |
| 2002/0133055 A1 | 9/2002 | Haindl |
| 2002/0143250 A1 | 10/2002 | Panescu et al. |
| 2002/0151766 A1 | 10/2002 | Shapland et al. |
| 2002/0151961 A1 | 10/2002 | Lashinski et al. |
| 2002/0161275 A1 | 10/2002 | Schweich, Jr. et al. |
| 2002/0169358 A1 | 11/2002 | Mortier et al. |
| 2002/0169359 A1 | 11/2002 | McCarthy et al. |
| 2002/0169360 A1 | 11/2002 | Taylor et al. |
| 2002/0169502 A1 | 11/2002 | Mathis |
| 2002/0169504 A1 | 11/2002 | Alferness et al. |
| 2002/0173694 A1 | 11/2002 | Mortier et al. |
| 2002/0183835 A1 | 12/2002 | Taylor et al. |
| 2002/0183836 A1 | 12/2002 | Liddicoat et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2002/0188170 A1 | 12/2002 | Santamore et al. |
| 2002/0188350 A1 | 12/2002 | Arru et al. |
| 2003/0004396 A1 | 1/2003 | Vanden Hock et al. |
| 2003/0009081 A1 | 1/2003 | Rogers et al. |
| 2003/0023132 A1 | 1/2003 | Melvin et al. |
| 2003/0028077 A1 | 2/2003 | Alferness et al. |
| 2003/0032979 A1 | 2/2003 | Mortier et al. |
| 2003/0045771 A1 | 3/2003 | Schweich, Jr. et al. |
| 2003/0045776 A1 | 3/2003 | Alferness et al. |
| 2003/0045896 A1 | 3/2003 | Murphy et al. |
| 2003/0050529 A1 | 3/2003 | Vidlund et al. |
| 2003/0050659 A1 | 3/2003 | Muphy et al. |
| 2003/0060674 A1 | 3/2003 | Gifford, III et al. |
| 2003/0065248 A1 | 4/2003 | Lau et al. |
| 2003/0069467 A1 | 4/2003 | Lau et al. |
| 2003/0078465 A1 | 4/2003 | Pai et al. |
| 2003/0078653 A1 | 4/2003 | Vesely et al. |
| 2003/0078671 A1 | 4/2003 | Lesniak et al. |
| 2003/0105519 A1 | 6/2003 | Fasol et al. |
| 2003/0120340 A1 | 6/2003 | Liska et al. |
| 2003/0130730 A1 | 7/2003 | Cohn et al. |
| 2003/0130731 A1 | 7/2003 | Vidlund et al. |
| 2003/0144697 A1 | 7/2003 | Mathis et al. |
| 2003/0149333 A1 | 8/2003 | Alferness |
| 2003/0153946 A1 | 8/2003 | Kimblad |
| 2003/0158570 A1 | 8/2003 | Ferrazzi |
| 2003/0166992 A1 | 9/2003 | Schweich, Jr. et al. |
| 2003/0171641 A1 | 9/2003 | Schweich, Jr. et al. |
| 2003/0171776 A1 | 9/2003 | Adams et al. |
| 2003/0171806 A1 | 9/2003 | Mathis et al. |
| 2003/0181928 A1 | 9/2003 | Vidlund et al. |
| 2003/0191538 A1 | 10/2003 | Buckberg et al. |
| 2003/0199733 A1 | 10/2003 | Shapland et al. |
| 2003/0212453 A1 | 11/2003 | Mathis et al. |
| 2003/0225454 A1 | 12/2003 | Mathis et al. |
| 2003/0229260 A1 | 12/2003 | Girard et al. |
| 2003/0229261 A1 | 12/2003 | Girard et al. |
| 2003/0229265 A1 | 12/2003 | Girard et al. |
| 2003/0229266 A1 | 12/2003 | Cox et al. |
| 2003/0233022 A1 | 12/2003 | Vidlund et al. |
| 2003/0233142 A1 | 12/2003 | Morales et al. |
| 2003/0236569 A1 | 12/2003 | Mathis et al. |
| 2004/0002719 A1 | 1/2004 | Oz et al. |
| 2004/0003819 A1 | 1/2004 | St. Goar et al. |
| 2004/0010305 A1 | 1/2004 | Alferness et al. |
| 2004/0015039 A1 | 1/2004 | Melvin |
| 2004/0015040 A1 | 1/2004 | Melvin |
| 2004/0015041 A1 | 1/2004 | Melvin |
| 2004/0019377 A1 | 1/2004 | Taylor et al. |
| 2004/0019378 A1 | 1/2004 | Hlavka et al. |
| 2004/0024286 A1 | 2/2004 | Melvin |
| 2004/0030382 A1 | 2/2004 | St. Goar et al. |
| 2004/0034271 A1 | 2/2004 | Melvin et al. |
| 2004/0039442 A1 | 2/2004 | St. Goar et al. |
| 2004/0039443 A1 | 2/2004 | Solem et al. |
| 2004/0044365 A1 | 3/2004 | Bachman |
| 2004/0049115 A1 | 3/2004 | Murphy et al. |
| 2004/0049116 A1 | 3/2004 | Murphy et al. |
| 2004/0059180 A1 | 3/2004 | Melvin |
| 2004/0059181 A1 | 3/2004 | Alferness |
| 2004/0059182 A1 | 3/2004 | Alferness |
| 2004/0059187 A1 | 3/2004 | Alferness |
| 2004/0059188 A1 | 3/2004 | Alferness |
| 2004/0059189 A1 | 3/2004 | Alferness |
| 2004/0059351 A1 | 3/2004 | Eigler et al. |
| 2004/0064014 A1 | 4/2004 | Melvin et al. |
| 2004/0073302 A1 | 4/2004 | Rourke et al. |
| 2004/0092962 A1 | 5/2004 | Thornton et al. |
| 2004/0093023 A1 | 5/2004 | Allen et al. |
| 2004/0098116 A1 | 5/2004 | Callas et al. |
| 2004/0102678 A1 | 5/2004 | Haindl |
| 2004/0102679 A1 | 5/2004 | Alferness et al. |
| 2004/0102839 A1 | 5/2004 | Cohn et al. |
| 2004/0102840 A1 | 5/2004 | Solem et al. |
| 2004/0111095 A1 | 6/2004 | Gordon et al. |
| 2004/0111101 A1 | 6/2004 | Chin |
| 2004/0122448 A1 | 6/2004 | Levine |
| 2004/0122512 A1 | 6/2004 | Navia et al. |
| 2004/0122513 A1 | 6/2004 | Navia et al. |
| 2004/0127980 A1 | 7/2004 | Kowalsky et al. |
| 2004/0127981 A1 | 7/2004 | Rahdert et al. |
| 2004/0127982 A1 | 7/2004 | Machold et al. |
| 2004/0133062 A1 | 7/2004 | Pai et al. |

| | | |
|---|---|---|
| 2004/0133069 A1 | 7/2004 | Shapland et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138526 A1 | 7/2004 | Guenst |
| 2004/0138744 A1 | 7/2004 | Lashinski et al. |
| 2004/0143323 A1 | 7/2004 | Chawla |
| 2004/0148019 A1 | 7/2004 | Vidlund et al. |
| 2004/0148020 A1 | 7/2004 | Vidlund et al. |
| 2004/0152947 A1 | 8/2004 | Schroeder et al. |
| 2004/0158123 A1 | 8/2004 | Reuter |
| 2004/0158321 A1 | 8/2004 | Jayaraman |
| 2004/0162610 A1 | 8/2004 | Liska et al. |
| 2004/0167374 A1 | 8/2004 | Schweich et al. |
| 2004/0167539 A1 | 8/2004 | Kuehn et al. |
| 2004/0171907 A1 | 9/2004 | Alferness et al. |
| 2004/0171908 A1 | 9/2004 | Alferness et al. |
| 2004/0171909 A1 | 9/2004 | Alferness |
| 2004/0172046 A1 | 9/2004 | Hlavka et al. |
| 2004/0176678 A1 | 9/2004 | Murphy et al. |
| 2004/0176679 A1 | 9/2004 | Murphy et al. |
| 2004/0176840 A1 | 9/2004 | Langberg et al. |
| 2004/0181121 A1 | 9/2004 | Alferness et al. |
| 2004/0181122 A1 | 9/2004 | Alferness et al. |
| 2004/0181123 A1 | 9/2004 | Alferness et al. |
| 2004/0181124 A1 | 9/2004 | Alferness |
| 2004/0181125 A1 | 9/2004 | Alferness et al. |
| 2004/0181126 A1 | 9/2004 | Buckberg et al. |
| 2004/0181238 A1 | 9/2004 | Zarbatany et al. |
| 2004/0186342 A1 | 9/2004 | Vanden Hock et al. |
| 2004/0186566 A1 | 9/2004 | Hindrichs et al. |
| 2004/0193191 A1 | 9/2004 | Starksen et al. |
| 2004/0193260 A1 | 9/2004 | Alferness et al. |
| 2004/0199183 A1 | 10/2004 | Oz et al. |
| 2004/0210304 A1 | 10/2004 | Seguin et al. |
| 2004/0225300 A1 | 11/2004 | Goldfarb et al. |
| 2004/0243227 A1 | 12/2004 | Starlksen et al. |
| 2004/0243229 A1 | 12/2004 | Vidlund et al. |
| 2004/0249452 A1 | 12/2004 | Adams et al. |
| 2004/0267329 A1 | 12/2004 | Raman et al. |
| 2005/0004428 A1 | 1/2005 | Cox et al. |
| 2005/0004666 A1 | 1/2005 | Alfieri et al. |
| 2005/0021056 A1 | 1/2005 | St. Goar et al. |
| 2005/0021057 A1 | 1/2005 | St. Goar et al. |
| 2005/0021135 A1 | 1/2005 | Ryan et al. |
| 2005/0027351 A1 | 2/2005 | Reuter et al. |
| 2005/0027353 A1 | 2/2005 | Alerness et al. |
| 2005/0027369 A1 | 2/2005 | Eldridge et al. |
| 2005/0033419 A1 | 2/2005 | Alferness et al. |
| 2005/0033446 A1 | 2/2005 | Deem et al. |
| 2005/0038507 A1 | 2/2005 | Alferness et al. |
| 2005/0043792 A1 | 2/2005 | Solem et al. |
| 2005/0049679 A1 | 3/2005 | Taylor et al. |
| 2005/0049698 A1 | 3/2005 | Bolling et al. |
| 2005/0055089 A1 | 3/2005 | Macoviak et al. |
| 2005/0060030 A1 | 3/2005 | Lashinski et al. |
| 2005/0065598 A1 | 3/2005 | Mathis et al. |
| 2005/0065601 A1 | 3/2005 | Lee et al. |
| 2005/0071000 A1 | 3/2005 | Liddicoat et al. |
| 2005/0075703 A1 | 4/2005 | Schroeder et al. |
| 2005/0075723 A1 | 4/2005 | Schroeder et al. |
| 2005/0075727 A1 | 4/2005 | Wheatley |
| 2005/0080402 A1 | 4/2005 | Santamore et al. |
| 2005/0080483 A1 | 4/2005 | Solem et al. |
| 2005/0085688 A1 | 4/2005 | Girard et al. |
| 2005/0095268 A1 | 5/2005 | Walsh et al. |
| 2005/0096740 A1 | 5/2005 | Langberg et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0113635 A1 | 5/2005 | Whayne et al. |
| 2005/0113811 A1 | 5/2005 | Houser et al. |
| 2005/0119519 A9 | 6/2005 | Girard et al. |
| 2005/0131533 A1 | 6/2005 | Alfier et al. |
| 2005/0149179 A1 | 7/2005 | Mathis et al. |
| 2005/0149180 A1 | 7/2005 | Mathis et al. |
| 2005/0149182 A1 | 7/2005 | Alferness et al. |
| 2005/0184122 A1 | 8/2005 | Hlavka et al. |
| 2005/0187619 A1 | 8/2005 | Mathis et al. |
| 2005/0192666 A1 | 9/2005 | McCarthy |
| 2005/0197528 A1 | 9/2005 | Vanden Hoek et al. |
| 2005/0197692 A1 | 9/2005 | Pal et al. |
| 2005/0197693 A1 | 9/2005 | Pai et al. |
| 2005/0209690 A1 | 9/2005 | Mathis et al. |
| 2005/0216077 A1 | 9/2005 | Mathis et al. |
| 2005/0216078 A1 | 9/2005 | Starksen et al. |
| 2005/0228217 A1 | 10/2005 | Alferness et al. |
| 2005/0261704 A1 | 11/2005 | Mathis et al. |
| 2005/0267574 A1 | 12/2005 | Cohn et al. |
| 2005/0272969 A1 | 12/2005 | Alferness et al. |
| 2006/0004443 A1 | 1/2006 | Liddicoat et al. |
| 2006/0030885 A1 | 2/2006 | Hyde |

FOREIGN PATENT DOCUMENTS

| | | |
|---|---|---|
| DE | 42 34 127 A1 | 5/1994 |
| DE | 296 19 294 U1 | 8/1997 |
| DE | 298 24 017 UY1 | 6/1998 |
| DE | 198 26 675 A1 | 3/1999 |
| DE | 199 47 885 A1 | 4/2000 |
| EP | 0 583 012 A1 | 2/1994 |
| EP | 0 792 621 A1 | 9/1997 |
| EP | 0 820 729 A1 | 1/1998 |
| EP | 1 129 736 A1 | 9/2001 |
| WO | WO 91/19465 A1 | 12/1991 |
| WO | WO 95/06447 A1 | 3/1995 |
| WO | WO 95/16407 A1 | 6/1995 |
| WO | WO 95/16476 A1 | 6/1995 |
| WO | WO 98/58598 A1 | 6/1995 |
| WO | WO 96/02197 A1 | 2/1996 |
| WO | WO 96/04852 A1 | 2/1996 |
| WO | WO 96/40356 A1 | 12/1996 |
| WO | WO 97/14286 A2 | 4/1997 |
| WO | WO 97/24082 A1 | 7/1997 |
| WO | WO 97/24083 A1 | 7/1997 |
| WO | WO 97/24101 A1 | 7/1997 |
| WO | WO 98/03213 A1 | 1/1998 |
| WO | WO 98/14136 A1 | 4/1998 |
| WO | WO 98/17347 A1 | 4/1998 |
| WO | WO 98/18393 A1 | 5/1998 |
| WO | WO 98/26738 A1 | 6/1998 |
| WO | WO 98/29041 A1 | 7/1998 |
| WO | WO 98/32382 A1 | 7/1998 |
| WO | WO 99/44969 A1 | 10/1998 |
| WO | WO 99/00059 A1 | 1/1999 |
| WO | WO 99/11201 A2 | 3/1999 |
| WO | WO 99/13777 A1 | 3/1999 |
| WO | WO 99/16350 A1 | 4/1999 |
| WO | WO 99/22784 A1 | 5/1999 |
| WO | WO 99/30647 A1 | 6/1999 |
| WO | WO 99/44534 A1 | 9/1999 |
| WO | WO 99/44680 A1 | 9/1999 |
| WO | WO 99/52470 A1 | 10/1999 |
| WO | WO 99/53977 A1 | 10/1999 |
| WO | WO 99/56655 A1 | 11/1999 |
| WO | WO 99/66969 A1 | 12/1999 |
| WO | WO 00/02500 A1 | 1/2000 |
| WO | WO 00/03759 A2 | 1/2000 |
| WO | WO 00/06026 A2 | 2/2000 |
| WO | WO 00/06028 A1 | 2/2000 |
| WO | WO 00/13722 A1 | 3/2000 |
| WO | WO 00/18320 A1 | 4/2000 |
| WO | WO 00/25842 A1 | 5/2000 |
| WO | WO 00/25853 A2 | 5/2000 |
| WO | WO 00/27304 A1 | 5/2000 |
| WO | WO 00/28912 A1 | 5/2000 |

| | | |
|---|---|---|
| WO | WO 00/28918 A1 | 5/2000 |
| WO | WO 00/36995 A2 | 6/2000 |
| WO | WO 00/42919 A1 | 7/2000 |
| WO | WO 00/42950 A2 | 7/2000 |
| WO | WO 00/42951 A1 | 7/2000 |
| WO | WO 00/45735 A1 | 8/2000 |
| WO | WO 00/60995 A2 | 10/2000 |
| WO | WO 00/61033 A1 | 10/2000 |
| WO | WO 00/62715 A1 | 10/2000 |
| WO | WO 00/62727 A1 | 10/2000 |
| WO | WO 01/00111 A1 | 1/2001 |
| WO | WO 01/03608 A1 | 1/2001 |
| WO | WO 01/19291 A1 | 3/2001 |
| WO | WO 01/19292 A1 | 3/2001 |
| WO | WO 01/21070 A1 | 3/2001 |
| WO | WO 01/21098 A1 | 3/2001 |
| WO | WO 01/21099 A1 | 3/2001 |
| WO | WO 01/21247 A1 | 3/2001 |
| WO | WO 01/54562 A2 | 3/2001 |
| WO | WO 01/95832 A1 | 3/2001 |
| WO | WO 01/26557 A1 | 4/2001 |
| WO | WO 01/28432 A1 | 4/2001 |
| WO | WO 01/49217 A2 | 7/2001 |
| WO | WO 01/50981 A1 | 7/2001 |
| WO | WO 01/54618 A1 | 8/2001 |
| WO | WO 01/54745 A2 | 8/2001 |
| WO | WO 01/67985 A1 | 9/2001 |
| WO | WO 01/70116 A1 | 9/2001 |
| WO | WO 01/78625 A1 | 10/2001 |
| WO | WO 01/85061 A2 | 11/2001 |
| WO | WO 01/91667 A2 | 12/2001 |
| WO | WO 01/95830 A2 | 12/2001 |
| WO | WO 01/95831 A2 | 12/2001 |
| WO | WO 02/11625 A2 | 2/2002 |
| WO | WO 02/13726 A2 | 2/2002 |
| WO | WO 02/19917 A1 | 3/2002 |
| WO | WO 02/28450 A2 | 4/2002 |
| WO | WO 02/30292 * 4/2002 | 600/16 |
| WO | WO 02/30292 A1 | 4/2002 |
| WO | WO 02/30335 A2 | 4/2002 |
| WO | WO 02/34167 A2 | 5/2002 |
| WO | WO 02/38081 A2 | 5/2002 |
| WO | WO 02/43617 A2 | 6/2002 |
| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 02/064035 A1 | 8/2002 |
| WO | WO 02/076284 A2 | 10/2002 |
| WO | WO 02/078576 A2 | 10/2002 |
| WO | WO 02/085251 A1 | 10/2002 |
| WO | WO 02/096275 A2 | 12/2002 |
| WO | WO 03/001893 A2 | 1/2003 |
| WO | WO 03/007778 A2 | 1/2003 |
| WO | WO 03/015611 A2 | 2/2003 |
| WO | WO 03/022131 A2 | 3/2003 |
| WO | WO 03/059209 A2 | 7/2003 |

OTHER PUBLICATIONS

McGoon, M.D. et al., "Correction of the univentricular heart having two atrioventricular valves," *The Journal of Thoracic and Cardiovascular Surgery*, vol. 74, No. 2, Aug. 1977, pp. 218-226.

Lev, M.D., et al., "Single (Primitive) Ventricle," *Circulation*, vol. 39, May 1969, pp. 577-591.

Westaby with Bosher, "Landmarks in Cardiac Surgery," 1997, pp. 198-199.

Shumacker, "Cardiac Aneurysms," *The Evolution of Cardiac Surgery*, 1992, pp. 159-165.

Feldt, M.D., "Current status of the septation procedure for univentricular heart," *The Journal of Thoracic and Cardiovascular Surgery*, vol. 82, No. 1, Jul. 1981, pp. 97-97.

Doty, M.D., "Septation of the univentricular heart," *The Journal of Thoracic and Cardiovascular Surgery*, vol. 78, No. 3, Sep. 1979, pp. 423-430.

Carpentier et al., "Myocardial Substitution with a Stimulated Skeletal Muscle: First Successful Clinical Case," Letter to the Editor, p. 1267, Sep. 25, 1996.

Ianuzzo et al., "Preservation of the Latissimus Dorsi Muscle During Cardiomyoplasty Surgery," *J. Card. Surg.*, 1996:11:99-108.

Ianuzzo et al., "On Preconditioning of Skeletal Muscle: Application to Dynamic Cardiomyoplasty," Invited Commentary, *J. Card. Surg.*, 1996:11:109-110.

Chachques et al., "Latissimus Dorsi Dynamic Cardiomyoplasty," *Ann. Thorac. Surg.*, 1989:47:600-604.

Moreira et al., "Latissimus Dorsi Cardiomyoplasty in the Treatment of Patients with Dilated Cardiomyopathy," Supplement IV Circulation, Sep. 25, 1996, 7 pgs.

Lucas et al., "Long-Term Follow-Up (12 to 35 Weeks) After Dynamic Cardiomyoplasty," *JACC*, vol. 22, No. 3, Sep. 1993:758-67.

Batista et al., "Partial Left Ventriculectomy to Improve Left Ventricular Function in End-Stage Heart Disease," *J. Card. Surg.*, 1996:11:96-98.

"Congestive Heart Failure in the United States: A New Epidemic" Data Fact Sheet, National Heart, Lung, and Blood Institute, National Institutes of Health, Dec. 9, 1996, pp. 1-6.

Kormos et al., "Experience with Univentricular Support in Mortally Ill Cardiac Transplant Candidates," *Ann. Thorac. Surg.*, 1990:49:261-71.

Wampler et al., "Treatment of Cardiogenic Shock with the Hemopump Left Ventricular Assist Device," *Ann. Thorac. Surg.*, 1991:52:506-13.

McCarthy et al., "Clinical Experience with the Novacor Ventricular Assist System," *J. Thorac. Cardiovasc. Surg.*, 1991:102-578-87.

Burnett et al., "Improved Survival After Hemopump Insertion in Patients Experiencing Postcardiotomy Cardiogenic Shock During Cardiopulmonary Bypass," From the Section of Transplantation, Division of Cardiovascular Surgery, Texas Heart Institute and St. Luke's Episcopal Hospital, Houston, Texas, dated even with or prior to Jan. 2, 1997, pp. 626-628.

Phillips et al., "Hemopump Support for the Failing Heart," From the Department of Cardiovascular Medicine and Surgery, Mercy Hospital Medical Center, Des Moines, Iowa, date even with or prior to Jan. 2, 1997, pp. 629-631.

Deeb et al., "Clinical Experience with the Nimbus Pump," From the University of Michigan Medical Center Section of Thoracic Surgery and Division of Cardiology, Ann Arbor, Michigan, date even with or prior to Jan. 2, 1997, pp. 632-636.

Bearnson et al., "Development of a Prototype Magnetically Suspended Rotor Ventricular Assist Device," *ASAIO Journal*, 1996, pp. 275-280.

Sakakibara et al., "A Muscle Powered Cardiac Assist Device for Right Ventricular Support: Total Assist or Partial Assist?," *Trans. Am.Soc. Artif. Intern. Organs*, vol. XXXVI, 1990, pp. 372-375.

Medtronic, Inc. 1996 Annual Shareholders Report, 79 pages.

ABIOMED, Inc. Annual Report 1996, 32 pages.

Press Release dated Sep. 16, 1996, "ABIOMED Wins $8.5 Million Federal Contract to Qualify its Artificial Heart for Human Trials," 5 pages.

Press Release dated Sep. 26, 1996, ABIOMED's Temporary Artificial Heart System Reaches 200 U.S. Medical Center Milestone,1 page.

Press Release dated May 17, 1996, "ABIOMED Receives FDA Approval to Expand Indications for Use of Cardiac Assist System," 1 page.

Press Release dated Oct. 3, 1995, "ABIOMED Wins $4.35 Million Contract from the National Heart, Lung and Blood Institutes to Develop Implantable Heart Booster," 1 page.

Press Release dated Sep. 29, 1995, "ABIOMED" Wins NIH Grant to Develop Calcification-Resistant Plastic Heart Valve,1 page.

Press Release dated Aug. 25, 1995, " ABIOMED Wins Research Grant from NIH to Develop Suturing Instrument for Abdominal surgery," 1 page.

Press Release dated Aug. 11, 1995, "ABIOMED Receives Grant from NIH to Develop Disposable Bearingless Centrifugal Blood Pump," 1 page.
Press Release dated Jun. 9, 1995, "ABIOMED Receives Grant from National Institutes of Health to Develop a Laser Welding Technique for Tissue Repair," 1 page.
Press Release dated Apr. 27, 1995, "ABIOMED's Temporary Artificial Heart System Reaches 1,000 Patient Milestone; BVS-5000 in More Than 100 U.S. Medical Centers," 1 page.
"Reversible Cardiomyopathy," *Thoratec's Heartbeat*, vol. 10.2, Aug. 1996, 4 pages.
Tsai et al., "Surfaces Modifying Additives for Improved Device-Blood Compatibility," *ASAIO Journal*, 1994, pp. 619-624.
Farrar et al., "A New Skeletal Muscle Linear-Pull Energy Convertor as a Power Source for Prosthetic Support Devices," *The Journal of Heart & Lung Transplantation*, vol. 11, No. 5, Sep. 1992, pp. 341-349.
Brochure entitled "Thoratec Ventricular Assist Device System-Because Heart Patients Come in All Sizes," date even with or prior to Jan. 2, 1997, 5 pages.
Press Release dated Oct. 3, 1994, "Heartmate System Becomes First Implantable Cardiac-Assist Device to be Approved for Commercial Sale in the U.S.," 2 pages.
Bocchi et al., "Clinical Outcome after Surgical Remodeling of Left Ventricle in Candidates to Heart Tranplantation with Idiopathic Dilated Cardiomypathy-Short Term Results," date even with or prior to Jan. 2, 1997, 1 page.
Bach et al., "Early Improvement in Congestive Heart Failure after Correction of Secondary Mitral Regurgitation in End-Stage Cardiomyopathy," *American Heart Journal*, Jun. 1995, pp. 1165-1170.
Schuler et al., "Temporal Response of Left Ventricular Performance to Mitral Valve Surgery," vol. 59, No. 6, Jun. 1979, pp. 1218-1231.
Huikuri, "Effect of Mitral Valve Replacement on Left Ventricular Function in Mitral Regurgitation," *Br. Heart J.*, vol. 49, 1983, pp. 328-333.
Pitarys II et al., "Long-Term Effects of Excision of the Mitral Apparatus on Global and Regional Ventricular Function in Humans," *JACC*, vol. 16, No. 3, Mar. 1, 1990, pp. 557-563.
Bolling et al., "Surgery for Acquired Heart Disease/Early Outcome of Mitral Valve Reconstruction in Patients with End-Stage Cardiomyopathy," *The Journal of Thoracic and Cardiovascular Surgery*, vol. 109, No. 4, Apr. 1995, pp. 676-683.
Masahiro et al., "Surgery for Acquired Heart Disease/Effects of Preserving Mitral Apparatus on Ventricular Systolic Function in Mitral Valve Operations in Dogs," *The Journal of Thoracic and Cardiovascular Surgery*, vol. 106, No. 6, Dec. 1993, pp. 1138-1146.
Dickstein et al., "Heart Reduction Surgery: An Analysis of the Impact on Cardiac Function," *The Journal of Thoracic and Cardiovacular Surgery*, vol. 113, No. 6, Jun. 1997, 9 pages.
McCarthy et al., "Early Results with Partial Left Ventriculectomy," From the Departments of Thoracic and Cardiovascular Surgery, Cardiology, and Transplant Center, Cleveland Clinic Foundation, Presented at the 77th Annual Meeting of the American Association of Thoracic Surgeons, May 1997, 33 pages.
Alonso-Lej, M.D., "Adjustable Annuloplasty for Tricuspid Insufficiency," *The Annals of Thoracic Surgery*, vol. 46, No. 3, Sep. 1988, 2 pages.
Kurlansky et al., "Adjustable Annuloplasty for Tricuspid Insufficiency," *Ann. Thorac. Surg.*, 44:404-406, Oct. 1987.
Savage, M.D., "Repair of left ventricular aneurysm," *The Journal of Thoracic and Cardiovascular Surgery*, vol. 104, No. 3, Sep. 1992, pp. 752-762.
Melvin, "Ventricular Radius Reduction Without Resection: A Computational Analysis," *ASAIO Journal*, 45:160-165, 1999.
Cox, "Left Ventricular Aneurysms: Pathophysiologic Obsrvations and Standard Resection," *Seminars in Thoracic and Cardiovascular Surgery*, vol. 9, No. 2, Apr. 1997, pp. 113-122.
Boyd et al., "Tricuspid Annuloplasty," *The Journal of Thoracic Cardiovascular Surgery*, vol. 68, No. 3, Sep. 1974, 8 pages.
Melvin, "Reduction of Ventricular Wall Tensile Stress by Geometric Remodeling Device", 1 page, undated.
Kay et al., "Surgical Treatment of Mitral Insufficiency", *The Journal of Thoracic Surgery*, 1955, 29:618-620.
Harken et al., "The Surgical Correction of Mitral Insufficiency", *The Journal of Thoracic Surgery*, 1954, 28:604-627.
Bailey et al., "Closed Intracardiac Tactile Surgery", *Diseases of the Chest*, 1952, XXII:1-24.
Sakakibara, "A Surgical Approach to the Correction of Mitral Insufficiency", *Annals of Surgery*, 1955, 142:196-203.
Glenn et al., "The Surgical Treatment of Mitral Insufficiency: The Fate of A Vascularized Transchamber Intracardiac Graft", *Annals of Surgery*, 1955, 141:4:510-518.
Kay et al., "Surgical Treatment of Mitral Insufficiency", *Surgery*, 1955, 37:5:697-706.
Bailey et al., "The Surgical Correction of Mitral Insufficiency By The Use of Pericardial Grafts", *The Journal of Thoracic Surgery*, 1954, 28:6:551-603.
Harken et al., "The Surgical Correction of Mitral Insufficency", *Surgical Forum*, 1953, 4:4-7.
Shumacker, Jr., "Attempts to Control Mitral Regurgitation", *The Evolution of Cardiac Surgery*, 1992, 203-210.
acorn cardiovacular, Inc., "Acorn Cardiovascular Summary", undated.
acorn cardiovascular, inc., "Acorn Cardiovascular Company Overview", undated.
Batista, MD et al., "Partial Left Ventriculectomy to Treat End-Stage Heart Disease", *Ann. Thorac. Surg.*, 64:634-8, 1997.
Melvin DB et al., Reduction of Ventricular Wall Tensile Stress by Geometric Remodeling Device, *Poster text, ASAIO* 1999.
Hayden et al., "Scintiphotographic Studies of Acquired Cardiovascular Disease," *Seminars in Nuclear Medicine*, vol. III, No. 2, Apr. 1973, pp. 177-190.
McCarthy, Transcription of Mar. 13, 2000 presentation given at ACC.
acorn cardiovascular, inc., "Acorn Cardiovascular Abstracts", Nov. 13, 2000.
Nation's First "Heart Jacket" Surgery to Treat Heart Failure Performed at HUP: Novel "Cardiac Support Device" Comes to America After Promising Results in Europe, Jun. 26, 2000.
acorn cardiovascular, inc., Acorn Cardiovascular Company Overview, undated, 1 page.
acorn cardiovascular, inc., Acorn Cardiovascular Company Overview, Jun. 2000.
acorn cardiovascular, inc., Acorn Cardiovascular Business Plan, May 2000.
acorn cardiovascular, inc., "Acorn Cardiovascular Highlights Abstracts", Mar. 10, 1999.
acorn cardiovascular, inc., "Acorn Cardiovascular Highlights Abstracts", Apr. 19, 1999.
acorn cardiovascular, inc., "Acorn Cardiovascular Highlights Abstracts", Oct. 1, 1999.
acorn cardiovascular, inc., "Acorn Cardiovascular Highlights Abstracts", Nov. 9, 1999.
Melvin DB, "Ventricular Radiu-Reduction Without Resection A Computational Assessment", undated.
Timek, Thomasz A., MD, et al, The Journal of Thoracic Surgery, vol. 123, No. 5 Surgery for Acquired Cardiovascular Disease, *Septal-lateral annular cinching abolishes acute ischemic mitral regurgitation*.
Timek, Thomasz A. et al, Department of Cardiothoracic Surgery and Division of Cardiovascular Medicine, Stanford University School of Medicine, Stanford, CA, *Septal-Lateral Annular Cinching ('SLAC') reduces Mitral Annular Size without Perturbing Normal Annular Dynamics*, 2002.
Hung, Judy MD et al., *Reverse Ventricular Remodeling Reduces Ischemic Mitral Regurgitation: Echo-Guided Device Application in the Beating Hear*, Circulation, www.circulation.org, Nov. 12, 2002.
Baim, Donald S., MD, Brigham and Women's Hospital, Harvard Medical School, *Percutaneous Treatment of Mitral Regurgitation*, 2005.
Dullum, Mercedes K.C., *Update on Restraint Devices for Congestive Heart Failure*, Abstract and copy of presentation slides given at Tech-Con 2005 for Society of Thoracic Surgeons, Jan. 23, 2005, 11 pages.

"Heart 'jacket' could help stop heart failure progress," *Clinica*, Jul. 10. 2000.

McCarthy et al., "Device Based Left Ventricular Shape Change Immediately Reduces Left Ventricular Volume and Increases Ejection Fraction in a Pacing Induced Cardiomyopathy Model in Dogs: A Pilot Study," JACC, Feb. 2000.

Alonso-Lej, *The Journal of Thoracic and Cardiovascular Surgery*, vol. 68, No. 3, Sep. 1974, p. 349.

US 6,197,052, 03/2001, Cosgrove et al. (withdrawn)

* cited by examiner

DEVICES AND METHODS FOR HEART VALVE TREATMENT

CROSS REFERENCE TO RELATED APPLICATIONS

This patent application claims the benefit of U.S. Provisional Patent Application No. 60/425,519, filed Nov. 12, 2002, entitled DEVICES AND METHODS FOR HEART VALVE TREATMENT to Vidlund et al., the entire disclosure of which is incorporated herein by reference (hereinafter referred to as "Vidlund et al., '519").

FIELD OF THE INVENTION

The present invention relates to devices and associated methods for treating and improving the performance of dysfunctional heart valves. More particularly, the invention relates to devices and methods that passively assist to reshape a dysfunctional heart valve to improve its performance.

BACKGROUND OF THE INVENTION

Various etiologies may result in heart valve insufficiency depending upon both the particular valve as well as the underlying disease state of the patient. For instance, a congenital defect may be present resulting in poor coaptation of the valve leaflets, such as in the case of a monocusp aortic valve, for example. Valve insufficiency also may result from an infection, such as rheumatic fever, for example, which may cause a degradation of the valve leaflets. Functional regurgitation also may be present. In such cases, the valve components may be normal pathologically, yet may be unable to function properly due to changes in the surrounding environment. Examples of such changes include geometric alterations of one or more heart chambers and/or decreases in myocardial contractility. In any case, the resultant volume overload that exists as a result of an insufficient valve may increase chamber wall stress. Such an increase in stress may eventually result in a dilatory process that further exacerbates valve dysfunction and degrades cardiac efficiency.

Mitral valve regurgitation often may be driven by the functional changes described above. Alterations in the geometric relationship between valvular components may occur for numerous reasons, including events ranging from focal myocardial infarction to global ischemia of the myocardial tissue. Idiopathic dilated cardiomyopathy also may drive the evolution of functional mitral regurgitation. These disease states often lead to dilatation of the left ventricle. Such dilatation may cause papillary muscle displacement and/or dilatation of the valve annulus. As the papillary muscles move away from the valve annulus, the chordae connecting the muscles to the leaflets may become tethered. Such tethering may restrict the leaflets from closing together, either symmetrically or asymmetrically, depending on the relative degree of displacement between the papillary muscles. Moreover, as the annulus dilates in response to chamber enlargement and increased wall stress, increases in annular area and changes in annular shape may increase the degree of valve insufficiency. Annular dilatation is typically concentrated on the posterior aspect, since this aspect is directly associated with the dilating left ventricular free wall and not directly attached to the fibrous skeleton of the heart. Annular dilatation also may result in a flattening of the valve annulus from its normal saddle shape.

Alterations in functional capacity also may cause valve insufficiency. In a normally functioning heart, the mitral valve annulus contracts during systole to assist in leaflet coaptation. Reductions in annular contractility commonly observed in ischemic or idiopathic cardiomyopathy patients therefore hamper the closure of the valve. Further, in a normal heart, the papillary muscles contract during the heart cycle to assist in maintaining proper valve function. Reductions in or failure of the papillary muscle function also may contribute to valve regurgitation. This may be caused by infarction at or near the papillary muscle, ischemia, or other causes, such as idiopathic dilated cardiomyopathy, for example.

The degree of valve regurgitation may vary, especially in the case of functional insufficiency. In earlier stages of the disease, the valve may be able to compensate for geometric and/or functional changes in a resting state. However, under higher loading resulting from an increase in output requirement, the valve may become incompetent. Such incompetence may only appear during intense exercise, or alternatively may be induced by far less of an exertion, such as walking up a flight of stairs, for example.

Conventional techniques for managing mitral valve dysfunction include either surgical repair or replacement of the valve or medical management of the patient. Medical management typically applies only to early stages of mitral valve dysfunction, during which levels of regurgitation are relatively low. Such medical management tends to focus on volume reductions, such as diuresis, for example, or afterload reducers, such as vasodilators, for example.

Early attempts to surgically treat mitral valve dysfunction focused on replacement technologies. In many of these cases, the importance of preserving the native subvalvular apparatus was not fully appreciated and many patients often acquired ventricular dysfunction or failure following the surgery. Though later experience was more successful, significant limitations to valve replacement still exist. For instance, in the case of mechanical prostheses, lifelong therapy with powerful anticoagulants may be required to mitigate the thromboembolic potential of these devices. In the case of biologically derived devices, in particular those used as mitral valve replacements, the long-term durability may be limited. Mineralization induced valve failure is common within ten years, even in younger patients. Thus, the use of such devices in younger patient groups is impractical.

Another commonly employed repair technique involves the use of annuloplasty rings. These rings originally were used to stabilize a complex valve repair. Now, they are more often used alone to improve mitral valve function. An annuloplasty ring has a diameter that is less than the diameter of the enlarged valve annulus. The ring is placed in the valve annulus and the tissue of the annulus sewn or otherwise secured to the ring. This causes a reduction in the annular circumference and an increase in the leaflet coaptation area. Such rings, however, generally flatten the natural saddle shape of the valve and hinder the natural contractility of the valve annulus. This may be true even when the rings have relatively high flexibility.

To further reduce the limitations of the therapies described above, purely surgical techniques for treating valve dysfunction have evolved. Among these surgical techniques is the Alfiere stitch or so-called bowtie repair. In this surgery, a suture is placed substantially centrally across the valve orifice joining the posterior and anterior leaflets to create leaflet apposition. Another surgical technique includes plication of the posterior annular space to reduce the cross-sectional area of the valve annulus. A limitation of each of these techniques is that they typically require opening the heart to gain direct access to the valve and the valve annulus. This generally necessitates the use of cardiopulmonary bypass, which may introduce additional morbidity and mortality to the surgical procedures. Additionally, for each of these procedures, it is very difficult to evaluate the efficacy of the repair prior to the conclusion of the operation.

Due to these drawbacks, devising effective techniques that could improve valve function without the need for cardiopulmonary bypass and without requiring major remodeling of the valve may be advantageous. In particular, passive techniques to change the shape of the heart chamber and/or associated valve and reduce regurgitation while maintaining substantially normal leaflet motion may be desirable. Further, advantages may be obtained by a technique that reduces the overall time a patient is in surgery and under the influence of anesthesia. It also may be desirable to provide a technique for treating valve insufficiency that reduces the risk of bleeding associated with anticoagulation requirements of cardiopulmonary bypass. In addition, a technique that can be employed on a beating heart would allow the practitioner an opportunity to assess the efficacy of the treatment and potentially address any inadequacies without the need for additional bypass support.

SUMMARY OF THE INVENTION

To address these needs, the present invention provides, in exemplary non-limiting embodiments, devices and methods for improving the function of a valve (e.g., mitral valve) by positioning an implantable device outside and adjacent the heart wall such that the device alters the shape of the heart wall acting on the valve. The implantable device may include two anchor ends with a interconnecting member connected therebetween. The anchor ends and the interconnecting member may be positioned on the outside of the heart. Optionally, a protrusion may be connected to the interconnecting member between the anchor ends. The anchor ends may be connected to the heart wall around the dysfunctional valve, and the interconnecting member may be tightened or cinched therebetween. Because the heart wall is generally curved, the act of cinching the interconnecting member between the attached anchor ends may cause the interconnecting member to apply an inward force against the heart wall acting on the dysfunctional valve, and/or may shorten the distance between the anchor ends and thus deform the heart wall inward to act on the dysfunctional valve. The inward force may act on any one of or any combination of valve structures (e.g., valve annulus, papillary muscles, etc.) and/or adjacent anatomical coronary structures. If a protrusion is utilized, it may be used to apply and focus additional force against the heart wall.

BRIEF DESCRIPTION OF THE DRAWINGS

Besides the structural and procedural arrangements set forth above, the invention could include a number of other arrangements, such as those explained hereinafter. It is to be understood that both the foregoing description and the following description are exemplary. The accompanying drawings are included to provide a further understanding of the invention and are incorporated in and constitute a part of this specification. The drawings illustrate exemplary embodiments of the invention and, together with the description, serve to explain certain principles. In the drawings.

DETAILED DESCRIPTION OF EXEMPLARY EMBODIMENTS

Figure 1A:
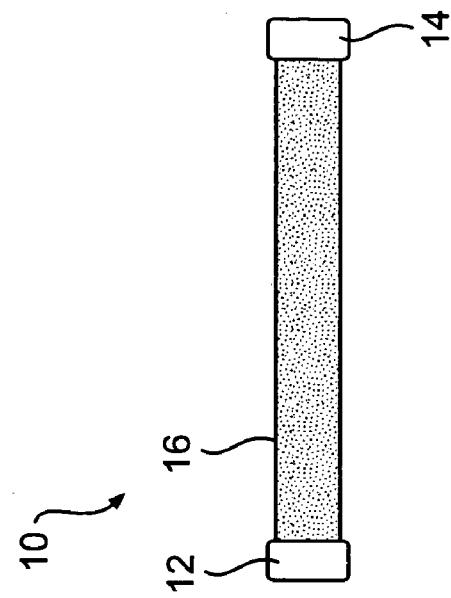
FIGS. 1A and 1B are bottom and side views, respectively, of an exemplary, non-limiting embodiment of an implantable device utilizing a protrusion.

The following detailed description should be read with reference to the drawings in which similar elements in different drawings are numbered the same. The drawings, which are not necessarily to scale, depict illustrative embodiments and are not intended to limit the scope of the invention.

The various aspects of the devices and methods described herein generally pertain to devices and methods for treating heart conditions, including, for example, dilatation, valve incompetencies, including mitral valve leakage, and other similar heart failure conditions. Each disclosed device may operate passively in that, once placed on the heart, it does not require an active stimulus, either mechanical, electrical, hydraulic, pneumatic, or otherwise, to function. Implanting one or more of the devices operates to assist in the apposition of heart valve leaflets to improve valve function.

In addition, these devices may either be placed in conjunction with other devices that, or may themselves function to, alter the shape or geometry of the heart, locally and/or globally, and thereby further increase the heart's efficiency. That is, the heart experiences an increased pumping efficiency through an alteration in its shape or geometry and concomitant reduction in stress on the heart walls, and through an improvement in valve function.

However, the devices disclosed herein for improving valve function can be "stand-alone" devices, that is, they do not necessarily have to be used in conjunction with additional devices for changing the shape of a heart chamber or otherwise reducing heart wall stress. It also is contemplated that a device for improving valve function may be placed relative to the heart without altering the shape of the chamber, and only altering the shape of the valve itself. In other words, the devices and methods described herein involve geometric reshaping of portions of the heart and treating valve incompetencies.

The devices and methods described herein offer numerous advantages over the existing treatments for various heart conditions, including valve incompetencies. The devices are relatively easy to manufacture and use, and the transluminal, transthoracic, and surgical techniques and tools for implanting the devices do not require the invasive procedures of current surgical techniques. For instance, these techniques do not require removing portions of the heart tissue, nor do they necessarily require opening the heart chamber or stopping the heart during operation. For these reasons, the techniques for implanting the devices disclosed herein also are less risky to the patient than other techniques. The less invasive nature of these techniques and tools may also allow for earlier intervention in patients with heart failure and/or valve incompetencies.

Although the methods and devices are discussed hereinafter in connection with their use for the mitral valve of the heart, these methods and devices may be used for other valves of the heart for similar purposes. One of ordinary skill in the art would understand that the use of the devices and methods described herein also could be employed for other valves of the heart. The mitral valve has been selected for illustrative purposes because a large number of the disorders occur in connection with the mitral valve.

The devices and methods described herein are discussed herein with reference to the human heart H, but may be equally applied to other animal hearts not specifically mentioned herein. For purposes of discussion and illustration, several anatomical features may be labeled as follows: left ventricle LV; right ventricle RV; left atrium LA; ventricular septum VS; right ventricular free wall RVFW; left ventricular free wall LVFW; atrioventricular groove AVG; mitral valve MV; tricuspid valve TV; aortic valve AV; pulmonary valve PV; papillary muscle PM; chordae tendeneae CT (or simply chordae); anterior leaflet AL; posterior leaflet PL; coaptation line CL; annulus AN; ascending aorta AA; thoracic aorta TA; azygos vein AZV; coronary sinus CS; cardiac vein CV; right coronary artery RCA; left anterior descending artery LAD; obtuse marginal artery OM; circumflex artery CFX; left lung LL; right lung RL; dermal layer DL; sternum ST; xiphoid XPH; diaphragm DPH; and vertebrae VRT.

General Description of Exemplary Implant Devices

Figure 1B:
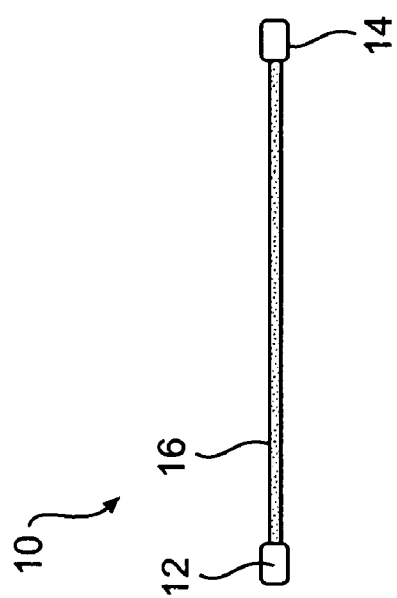
Figure 1C:
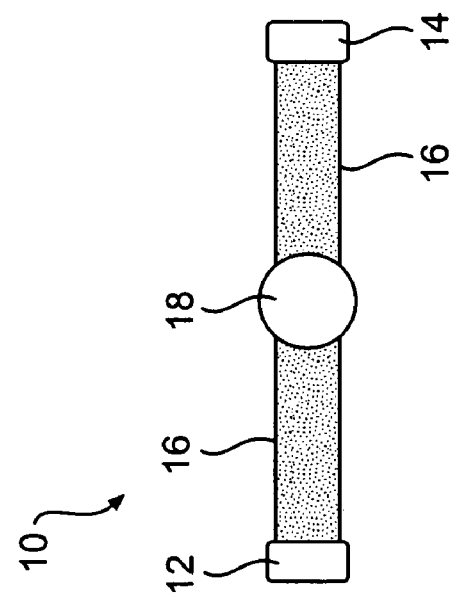
FIGS. 1C and 1D are bottom and side views, respectively, of an exemplary, non-limiting alternative embodiment of an implantable device without a protrusion.
Figure 1D:
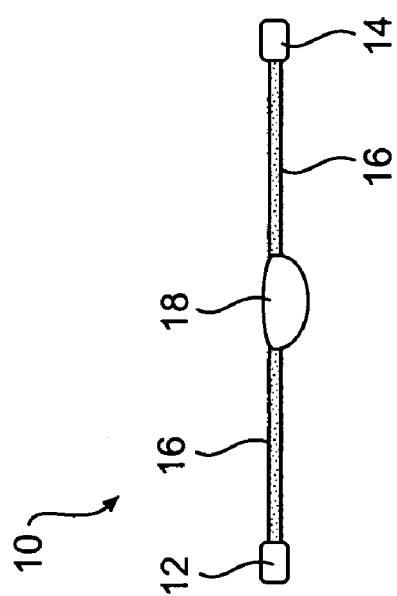

With reference to FIGS. 1A and 1B, a generic implantable device 10 is shown schematically. The implantable device 10 may generally include two or more anchor ends 12/14 with a interconnecting member 16 connected therebetween. The anchor ends 12/14 may be configured to permanently or releasably attach to the outside of the heart wall. The interconnecting member 16 may be selectively tightened or loosened to correspondingly affect the tension between the anchor ends 12/14. A protrusion 18 may be connected to the interconnecting member 16 between the anchor ends 12/14. Alternatively, as shown in FIGS. 1C and 1D, the implantable device 10 may utilize anchor ends 12/14 and interconnecting member 16 alone, without the use of a protrusion 18. With or without protrusion 18, the interconnecting member may be generally flexible to conform to the outer surface of the heart. Protrusion 18 may alternatively be referred to as a space filling member or a focal member. Interconnecting member 16 may alternatively be referred to as an elongate member or as a tension member.

The position of the protrusion 18 may be adjusted relative to the anchor ends 12/14. To accommodate such adjustment, the interconnecting member 16 may be fixedly connected to one or both of the anchor ends 12/14 and adjustably connected to the protrusion 18. Alternatively, the interconnecting member 16 may be fixedly connected to the protrusion 18 and adjustably connected to one or both of the anchor ends 12/14. In both instances, the length of the interconnecting member 16 between the protrusion 18 and the anchor ends 12/14 may be adjusted to change the position of the protrusion 18 relative to the anchor ends 12/14.

The anchors 12/14 serve to secure the ends of the interconnecting member 16 to the heart wall. The anchors 12/14 may comprise vacuum cups with tissue piercing pins for securement as described in more detail with reference to FIGS. 5A-5D. The anchors 12/14 may be remotely activated as described with reference to FIGS. 6 and 7. The anchors 12/14 may selectively connect to some tissue (e.g., epicardium, myocardium) while remaining free of other tissue (e.g. pericardium). Various alternative anchor embodiments are envisioned, such as tines, screws, sutures, adhesives, etc., and/or a tissue in-growth promoting material (e.g., Dacron fabric). For example, the anchors 12/14 may comprise tines that extend through the epicardium and into the myocardium, and optionally extend through the endocardium into a heart chamber. Additional alternative anchor embodiments are described by Vidlund et al., '519.

The interconnecting member 16 may be fixed or selectively fixed (i.e., adjustable) to each of the anchors 12/14 and/or the protrusion 18 as described above. The interconnecting member may be made fixed or adjustable using, for example, a lock pin technique as described in more detail with reference to FIGS. 5A-5D.

As an alternative to interconnecting member 16, or in conjunction with interconnecting member 16, pericardial tissue may be used to connect the anchor ends 12/14 and protrusion 18 (if used). For example, a first anchor end 12 may be fixedly secured to both the epicardium and the pericardium using an anchor device with open top and bottom surfaces as described in Vidlund et al., '519. The second anchor end 14 may be secured to epicardium, and the protrusion 18 may be secured to the pericardium (by using an anchor device for the protrusion 18). The interconnecting member 16 may be fixedly connected to the protrusion 18 and adjustably connected to the second anchor end 14 (or visa-versa) such that the position of the protrusion 18 may be adjusted (e.g., cinched) relative to the second anchor end 14. By virtue of the common pericardial connection between the first anchor 12 and the protrusion 18, cinching the interconnecting member 16 between the protrusion 18 and the second anchor 14 also causes cinching between the protrusion 18 and the first anchor 12, without requiring the interconnecting member 16 to be connected to the first anchor 12.

Figure 5A:
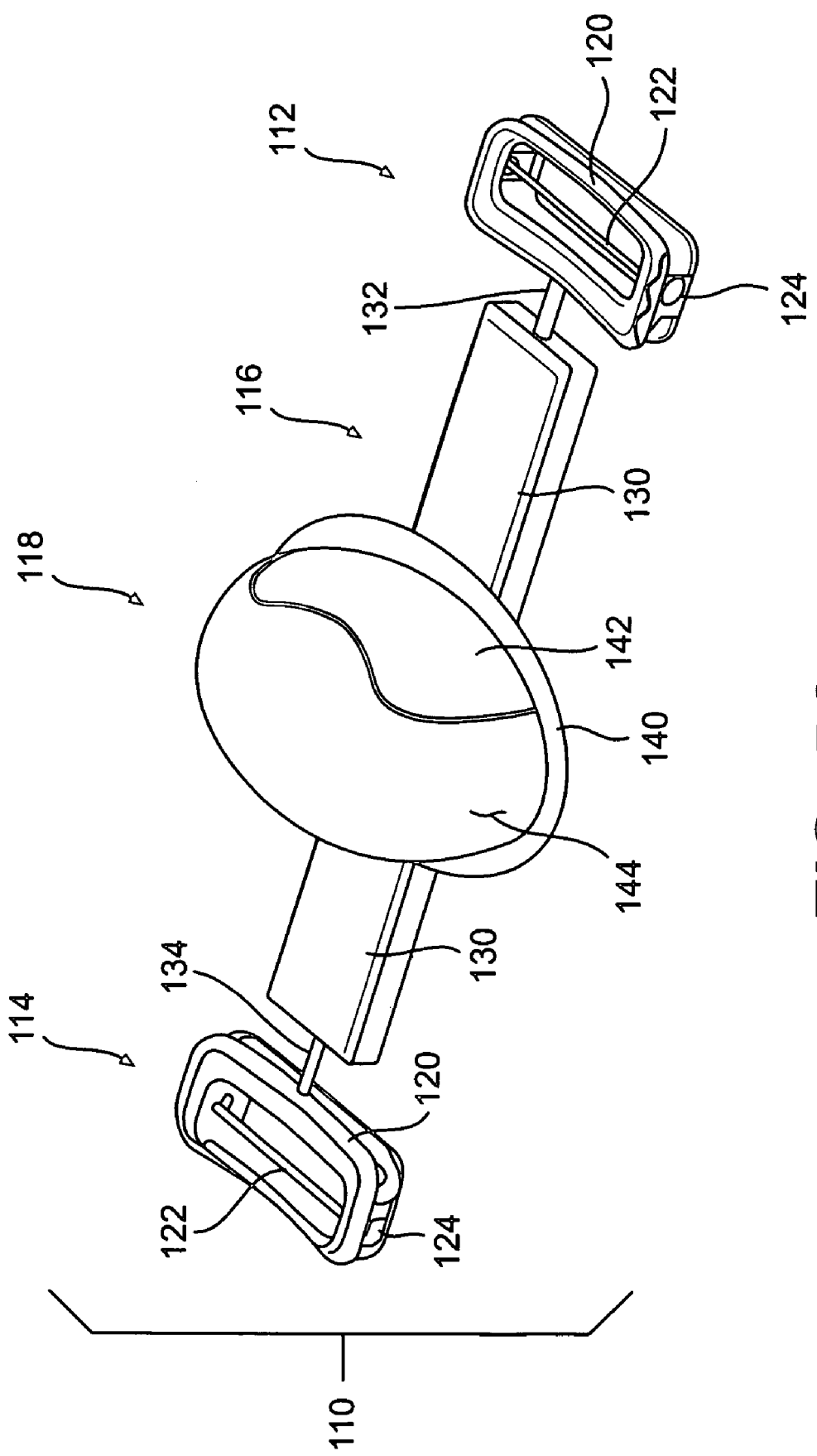
FIGS. 5A-5D are perspective views of more specific embodiments of implantable devices of the present invention.

The interconnecting member 16 may be elongate and will normally be in tension when implanted. The interconnecting member may comprise a flexible and biocompatible multifilament braid in the form of a string or strap, for example. If a string or chord is used, for example, an atraumatic pad (as seen in FIG. 5A) may be disposed on the interconnecting member 16 to avoid stress concentration on the heart wall by the interconnecting member 16.

The interconnecting member 16 may be formed as described in U.S. Pat. No. 6,537,198 to Vidlund et al., the entire disclosure of which is incorporated herein by reference. In particular, the interconnecting member 16 may comprise a composite structure including an inner cable to provide mechanical integrity and an outer covering to provide biocompatibility. The inner cable of interconnecting member 16 may have a multifilament braided-cable of high performance polymeric fibers such as ultra high molecular weight polyethylene available under the trade names Spectra™ and Dyneema™, polyester available under the trade name Dacron™, or liquid crystal polymer available under the trade name Vectran™. The filaments forming the inner cable may be combined, for example, in yarn bundles of approximately 50 individual filaments, with each yarn bundle being approximately 180 denier, and two bundles may be paired together (referred to as 2-ply) and braided with approximately 16 total bundle pairs with approximately 20 to 50 picks per inch (number of linear yarn overlaps per inch).

The outer covering surrounding the inner cable of the interconnecting member 16 may provide properties that facilitate sustained implantation, and may thus be formed of a material that is biocompatible and allows for tissue ingrowth. For example, the outer covering surrounding the inner cable of the interconnecting member 16 may be made of a polyester material such as Dacron or ePTFE. If an atraumatic pad is used, it may be formed of, coated with, or covered by the same or similar material as the outer covering of the interconnecting member to promote tissue in-growth for additional anchoring effect. For example, the atraumatic pad may be formed of ePTFE which is biocompatible, promotes tissue in-growth, and conserves cross-sectional size and shape despite elongation.

The protrusion 18 may comprise a balloon, plug, or other mechanical spacer or structure, and may be fixedly or adjustably connected to the interconnecting member 16. The protrusion 18 may be centered between the anchors 12/14, or may be eccentrically positioned therebetween. One or more protrusions 18 may be used, and the protrusions may have various geometries depending on the desired allocation of forces acting on the heart wall. The protrusion 18 may be coated or covered by a tissue in-growth promoting material to secure the protrusion to the heart wall in the desired position, and the material may be highly elastic or otherwise stretchable to permit expansion of the protrusion 18. Examples of suitable materials include ePTFE and polyester knits.

Description of Exemplary Implant Positions and Functions

Figure 2A:
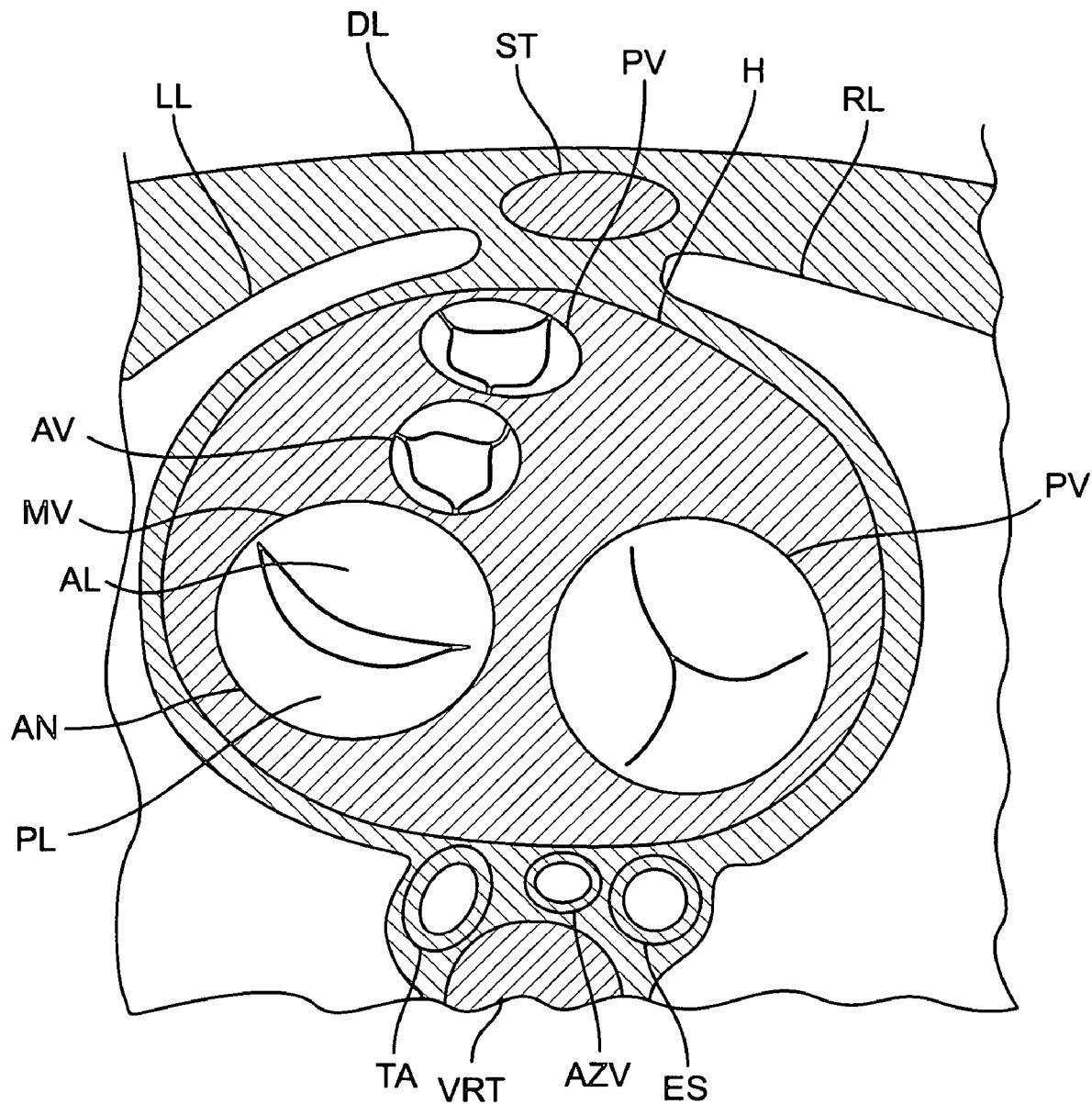
FIGS. 2A-2C are sectional views of a patient's trunk at the level of the mitral valve of the heart, showing an example of where the implantable devices may be positioned in the short axis view, and showing the effects of the implantable devices on mitral valve function.
Figure 2B:
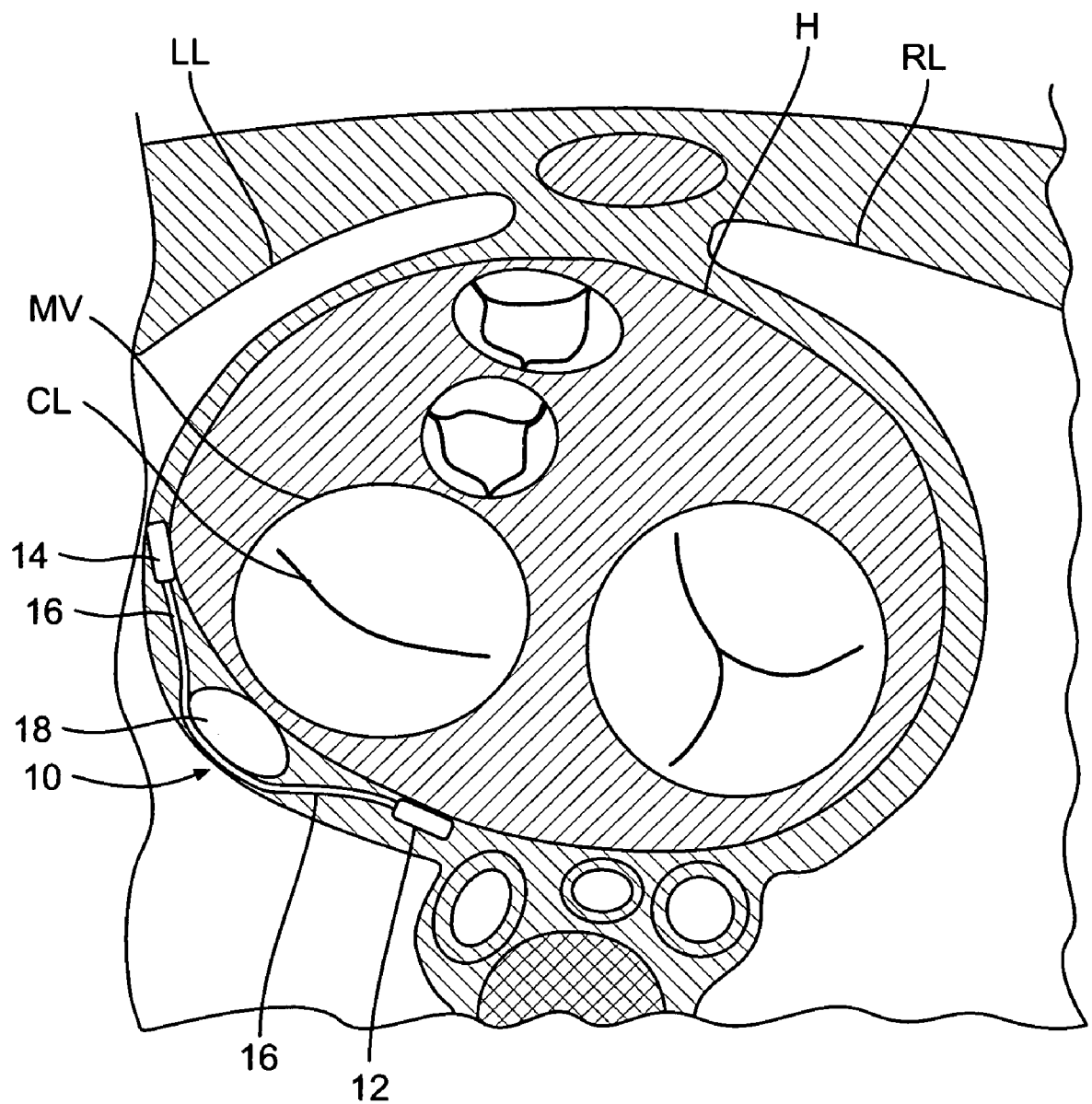
Figure 2C:
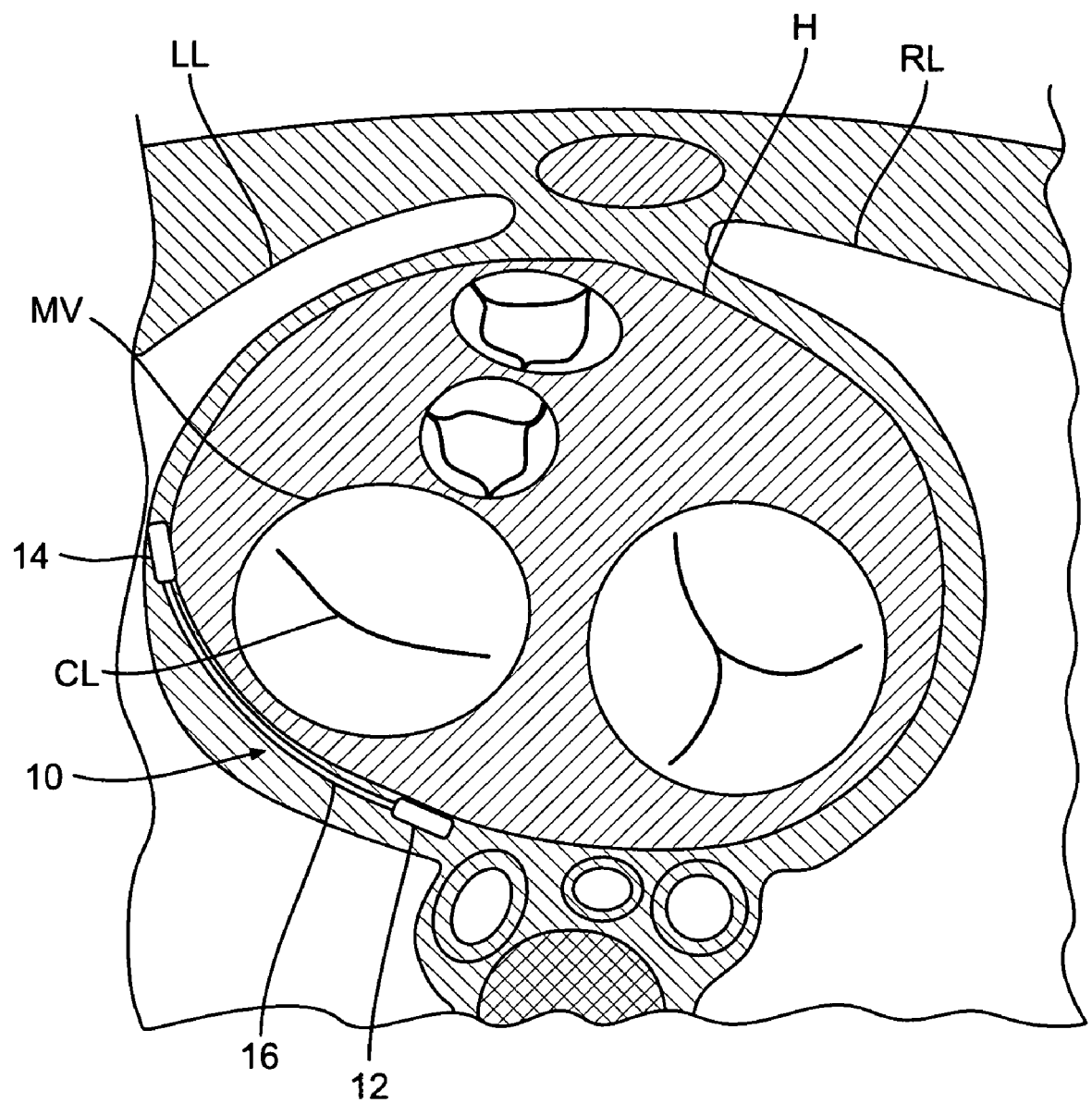

With reference to FIGS. 2A-2C, cross sectional views of a patient's trunk at the level of the mitral valve MV of the heart H show the effects of implantable device 10 on mitral valve MV function. As seen in FIG. 2A, an incompetent mitral valve MV is shown during systole, as rendered incompetent by, for example, a dilated valve annulus AN, a displaced papillary muscle PM due to ventricular dilation or other mechanism. With reference to FIGS. 2B and 2C, the implantable device 10 may be positioned outside and adjacent the heart wall such that the device 10 acts on the mitral valve MV. As seen in FIGS. 2B and 2C, the formerly incompetent mitral valve MV is shown during systole as corrected with implantable device 10. The implantable device 10 causes inward displacement of a specific portion of the heart wall adjacent the mitral valve MV resulting in re-configuration and re-shaping of the annulus AN and/or the papillary muscles PM, thus providing more complete closure of the mitral valve leaflets AL/PL during systole, as shown by closed coaptation line CL in FIGS. 2B and 2C.

The implantable device 10 may affect MV function by acting on the adjacent heart wall in several different modes. For example, in one mode of operation, the protrusion 18 (or the interconnecting member 16 if no protrusion is used) of the implantable device 10 may apply or focus an inward force against the heart wall acting on the MV. The back-up force (i.e., the substantially equal and opposite force to the inward force) may be provided by the interconnecting member 16 as fixed to the heart wall by the anchor ends 12/14, the anatomical structure behind the protrusion 18, or a combination thereof. In an alternative mode of operation, the implantable device 10 may act to cinch, compress or otherwise deform the heart wall surrounding the posterior aspect of the mitral valve MV by shortening the circumferential length thereof. In another alternative mode of operation, the implantable device 10 acts to both apply an inward force and cause circumferential shortening. In each of these modes of operation, the inward force and/or circumferential shortening may be applied throughout the cardiac cycle, or may only act during a portion of the cardiac cycle such as during systole.

The implantable device 10 may be implanted in a number of different positions, a select few of which are described herein for purposes of illustration, not necessarily limitation. Generally, the implantable device 10 may be positioned outside the epicardium of the heart wall adjacent the mitral valve MV, such as between the epicardium and pericardium, or between the pericardium and the pleural sac. Also generally, to maximize the effectiveness of the inward force, the implantable device 10 may be positioned to create a normal force against the heart wall that is generally orthogonal to the coaptation line CL formed by the leaflets PL/AL. This may be achieved, for example, by positioning the device 10 in a posterior-lateral projection of the mitral valve MV generally orthogonal to the middle tangent of the coaptation line CL as shown in FIGS. 2B and 2C.

Figure 3:
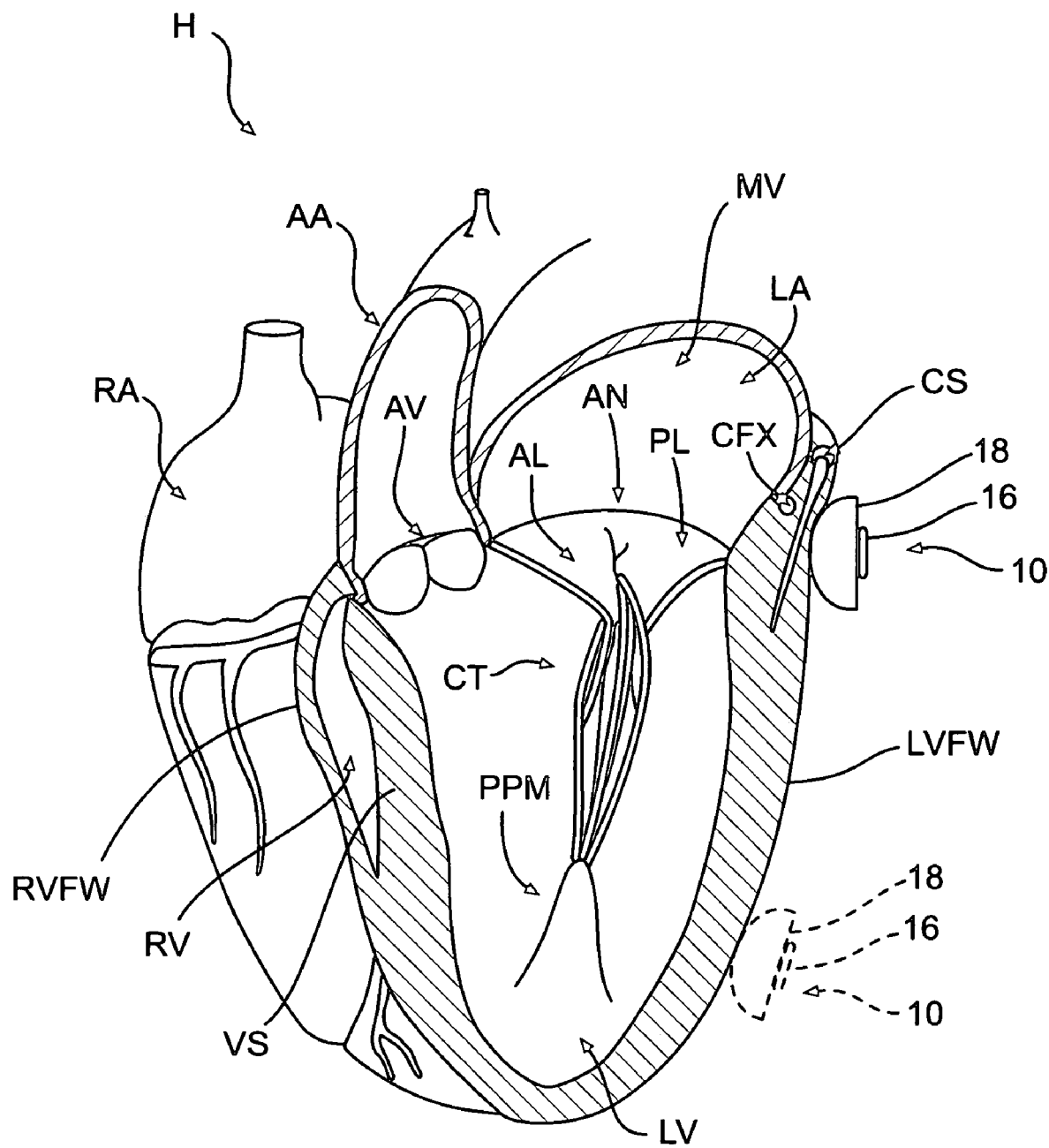
FIG. 3 is a sectional view of a patient's heart bisecting the mitral valve, showing an example of where the implantable devices may be positioned in the long axis view.

A variety of long axis and short axis positions are contemplated and the particular combination may be selected to have the desired effect. In the short axis view as seen in FIGS. 2B and 2C, the implantable device 10 may extend along all of, a portion of, or beyond the posterior-lateral projection of the mitral valve MV. In the long axis view as seen in FIG. 3, the implantable device 10 may extend along all of, a portion of, or beyond the posterior-lateral projection of the mitral valve MV structures, including the papillary muscles PM, the chordae CT, the leaflets PL/AL, and the annulus AN. For example, the implantable device 10 may be positioned adjacent the annulus AN (e.g., extending slightly above and below the annulus AN near the AV groove), or adjacent the papillary muscles PM (e.g., extending slightly above and below the papillary muscles PM).

Figure 4:
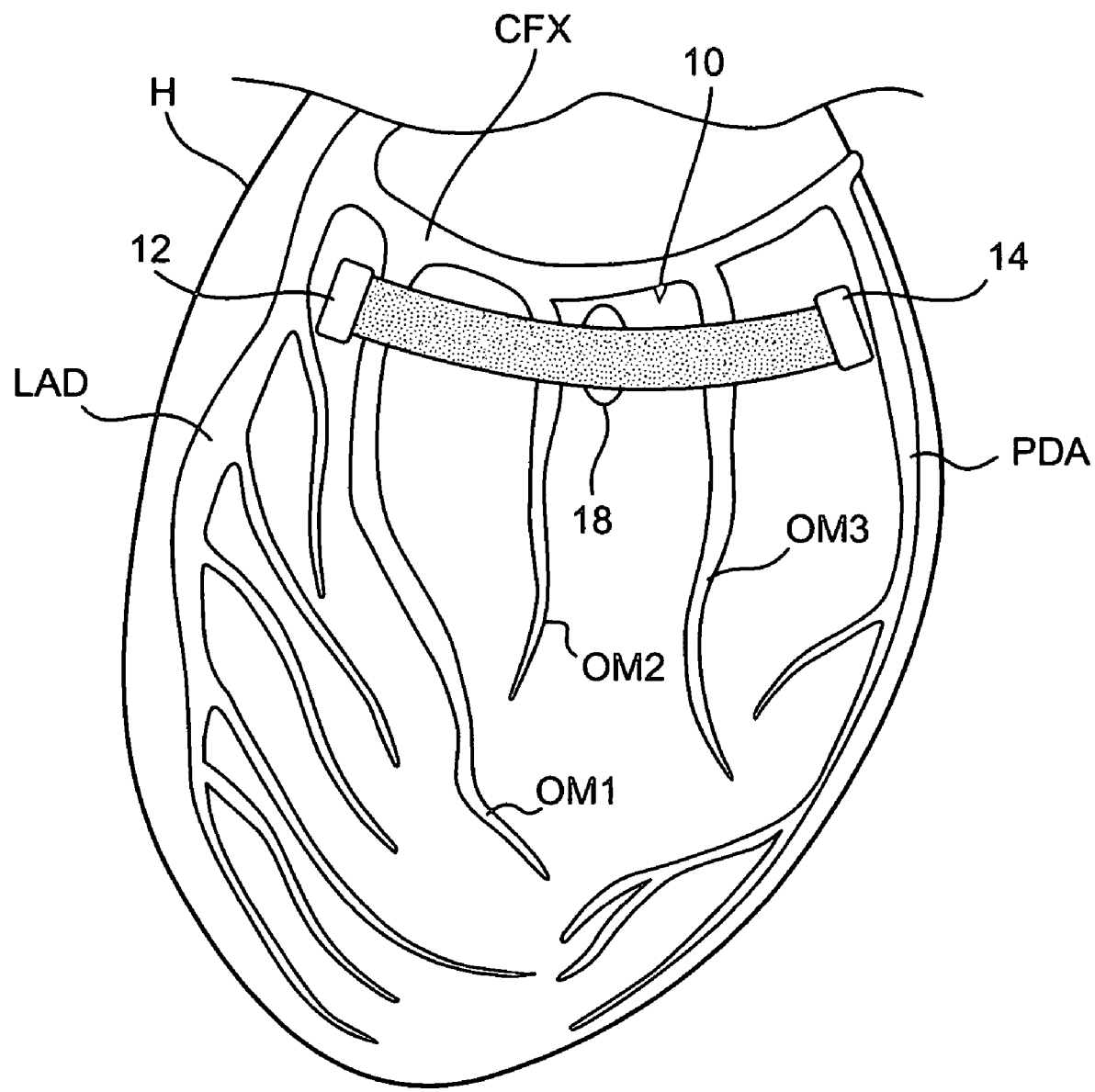
FIG. 4 is an angiographic illustration of a patient's heart, showing an example of where the implantable devices may be positioned relative to the coronary arteries.

To avoid compression of the coronary arteries which typically reside near the surface of the heart wall, the implantable device 10 may have relatively small contact areas selected and positioned to establish contact with the heart wall while avoiding key anatomical structures. For example, as shown in FIG. 4, the implantable device 10 may be positioned with the first anchor 12 positioned between the proximal left anterior descending artery LAD and the proximal first obtuse marginal OM1, the protrusion positioned inferior of the circumflex artery CFX between the second obtuse marginal OM2 and third obtuse marginal OM3, and the second anchor 14 positioned adjacent the posterior descending artery PDA. Alternatively, the implantable device 10 may have a relatively large surface area in contact with the heart wall to distribute the applied forces and avoid force focal points, particularly on the cardiac vasculature.

Description of Exemplary Delivery Techniques and Approaches

The implantable device 10 may be implanted using one or a combination of various methods and approaches. Generally, these delivery methods may be utilized to implant the device 10 in the pericardial space adjacent the posterior projection of the mitral valve MV. There are a number of different approaches and techniques for positioning the implantable device 10 as such, and these generally include surgical, transluminal and transthoracic techniques. For purposes of illustration, not necessarily limitation, an anterior transthoracic (subxiphoid) approach is described in more detail with reference to FIG. 11. Examples of other suitable approaches are described in more detail by Vidlund et al., '519.

Exemplary Embodiments of Implant Devices

With reference to FIGS. 5A-5D, perspective views of implantable devices 110, 210, 610 and 710, respectively, are shown. Note that the side of the device 110/210/610 that faces the heart wall when implanted is the top side in the illustration. Devices 110, 210, 610 and 710 are further exemplary embodiments of the generic embodiment of implantable device 10 described previously, in which similar components have similar nomenclature, and such may be made, used and function in the same or similar manner.

As seen in FIG. 5A, implantable device 110 includes a first anchor 112, a second anchor 114, a interconnecting member 116, and an optional protrusion 118. Each of the first anchor 112, second anchor 114, interconnecting member 116, and protrusion 110 may be loaded with a radiopaque material to render the visible under x-ray. In this embodiment, the interconnecting member 116 may comprise cables 132 and 134, and the anchors 112 and 114 may comprise vacuum cups 120 with tissue piercing pins 122, as will be described in more detail hereinafter. The anchor members 112 and 114 may be selectively attached, released and re-attached to the heart, and the protrusion 118 may be selectively adjusted relative to the anchor members 112 and 114 by adjusting the respective lengths of the interconnecting member 116. The ends of the interconnecting member 116 may be fixedly attached to the anchors 112 and 114, and adjustment of the length of the interconnecting member 116 is provided by a locking mechanism 160 as seen in and described with reference to FIG. 6A.

The anchors 112 and 114 may comprise a vacuum cup 120 with a tissue piercing pin 122 extending through the interior thereof. The cup 120 may be injection molded, for example, of a suitable biocompatible material such as PEEK, HDPE or PTFE, and the piercing pins 122 may be formed of stainless steel, for example. The piercing pins 122 are slidingly received in two bores disposed in the walls of the cup 120. A locking mechanism such as mating geometry between the bores and the pins may be used to lock the pins in the pierced position as shown. A port 124 in communication with the interior of the cup 120 is provided for releasable connection to an anchor catheter 400 as shown and described with reference to FIGS. 6A and 6B.

Each cup 120 has a rim that conforms to the epicardial surface of the heart wall such that vacuum applied to the cup 120 by the anchor catheter 400 via port 124 draws the epicardial surface of the heart into the interior of the cup. With the epicardial tissue drawn inside the cup by the vacuum, the tissue piercing pin 122 may be advanced to pierce through the heart tissue and lock in the pierced position as shown. A lock mechanism such as illustrated in FIG. 5E may be used to secure pins 122. In this manner, the anchors 112 and 114 may be secured to the outside surface of the heart wall.

The protrusion 118 includes a base 140, an inflatable balloon 142 mounted to the base 140, and an outer covering 144 (shown partially cut-away) extending over the balloon 142. The base 140 may be connected to a locking mechanism 160 (not visible) located on the opposite side of the balloon 142, which in turn is connected to the interconnecting member 116. The base 140 may comprise a flexible or semi rigid polymeric material, and the balloon 142 may comprise a compliant or non-complaint polymeric material conventionally used for implantable balloons. Outer covering 144 may comprise a material that promotes tissue in-growth to provide additional anchoring stability over time. The balloon 142 may be pre-filled, or may be filled during implantation, with a liquid that may solidify (cured) over time. To facilitate inflation of the balloon 142, the interior of the balloon 142 may be in fluid communication with an inflation catheter via a lumen (not visible) extending through the locking mechanism 160 and the base 140 as described with reference to FIG. 6A.

The interconnecting member 116 may comprise two multifilament braided cables 132 and 134. One end of each cable 132 and 134 may be fixedly connected to the anchors 112 and 114, respectively, and the other ends of the cables 132 and 134 may be adjustably connected together by a locking mechanism 160 (not visible) attached to the base 140 of the protrusion 118. The cables 132 and 134 may extend through a pair of atraumatic pads 130 that are secured to the base 140 of the protrusion 118.

Figure 5B:
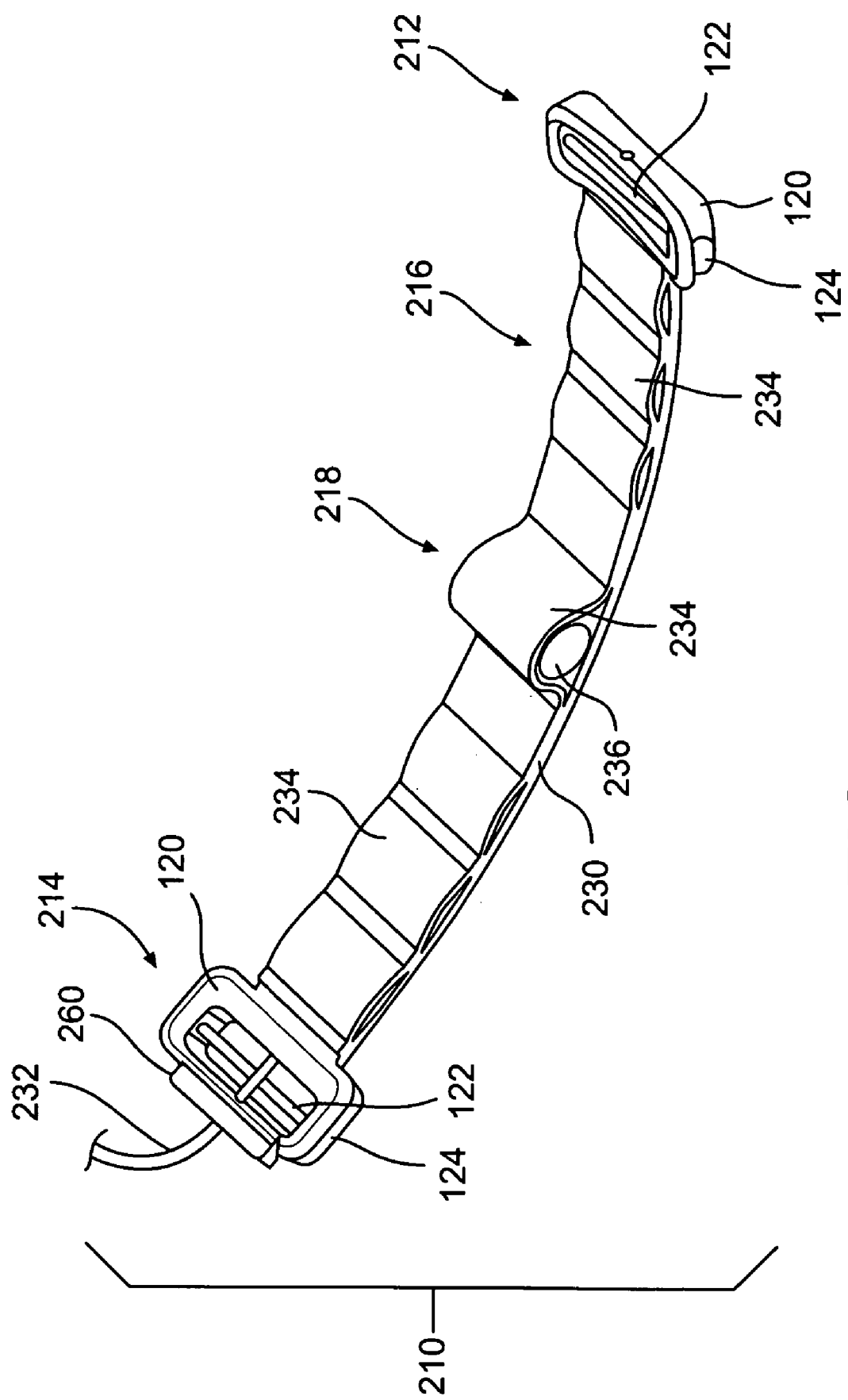

As seen in FIG. 5B, implantable device 210 includes a first anchor 212, a second anchor 214, a interconnecting member 216, and a protrusion 218. In this embodiment, the interconnecting member 216 includes a cable 232 extending through a strap 230, with one end of the cable 232 fixedly connected to first anchor 212, and the other end extending through second anchor 214 to which the cable may be selectively locked to adjust the length of the interconnecting member 216. A locking mechanism 260, similar to the locking mechanism 160 discussed with reference to FIG. 6A, may be connected to the second anchor 214 for selective tightening of and fixation to cable 232. Otherwise, anchors 212 and 214 may be the same as anchors 112 and 114 described previously.

Strap 230 may vary in length as a function of the length of the cable 232, and includes a plurality of pockets 234 that may be selectively filled with one or more plugs 236 to serve as the protrusion 218, or the pockets 234 may remain empty. For example, selection of the pockets 234 to fill with plugs 236 may be made apply an inward force against the heart wall while avoiding or jumping over coronary arteries residing near the surface of the heart wall. Strap 230 may comprise a woven polymeric material as polyester, and the plug 236 may comprise a solid polymeric material such as PEEK, silicone, HDPE, PTFE or ePTFE.

Figure 5C:
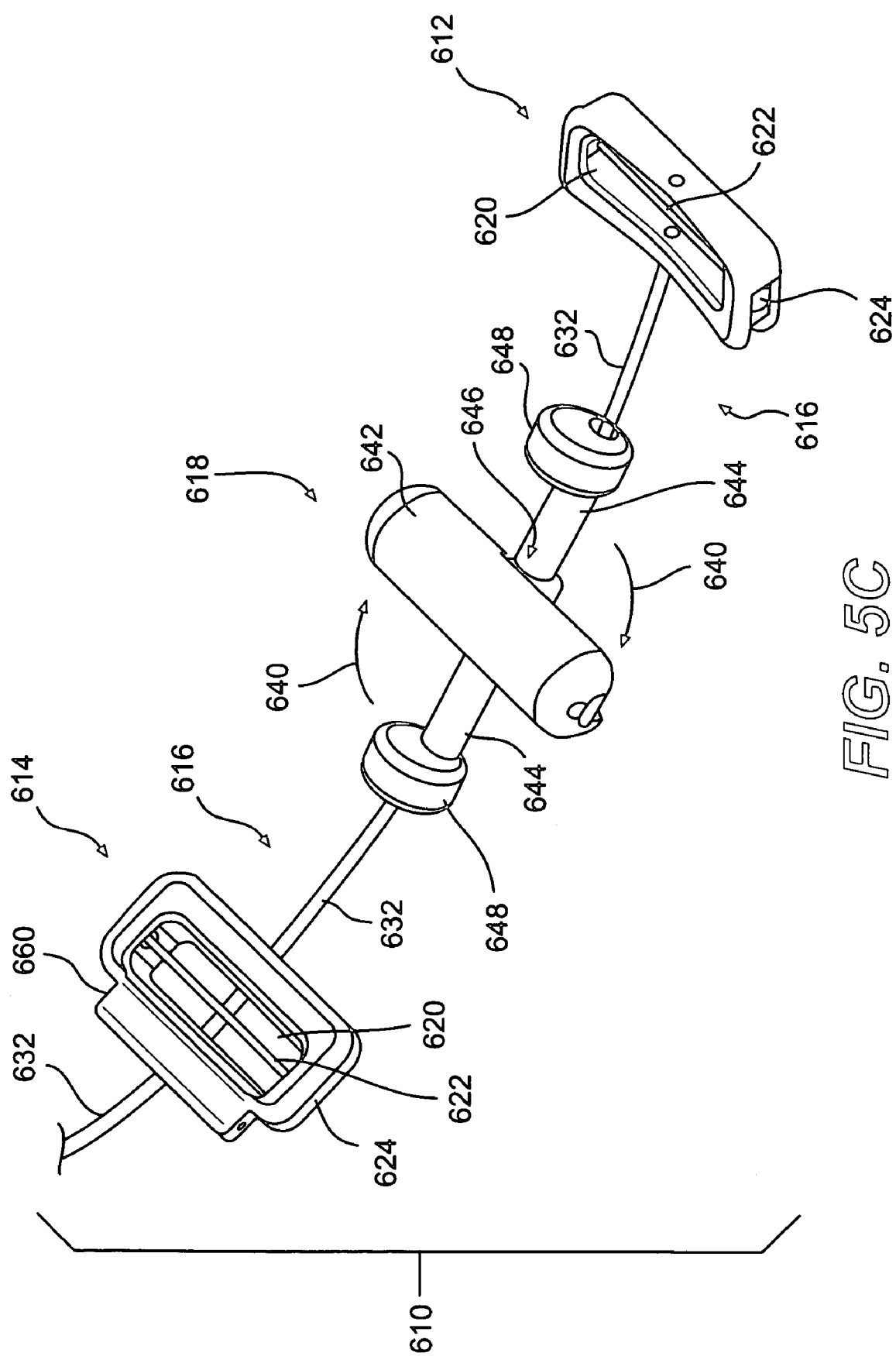

As seen in FIG. 5C, implantable device 610 includes a first anchor 612, a second anchor 614, a interconnecting member 616, and a protrusion 618. In this embodiment, the interconnecting member 616 includes cable 632 extending through protrusion 618, with one end of the cable 632 fixedly connected to first anchor 612, and the other end extending through second anchor 614 to which the cable may be selectively locked to adjust the length of the interconnecting member 616. A locking mechanism 660, similar to the locking mechanism 160 discussed with reference to FIGS. 6A and 5E, may be connected to the second anchor 614 for selective tightening of and fixation to cable 632. Anchors 612 and 614 include interior cavities 620 in fluid communication with a vacuum source to accommodate heart tissue for securement thereto by tissue piercing pins 622. A port 624 in communication with the interior of the cup 620 is provided for releasable connection to an anchor catheter 400 or 800 as shown and described with reference to FIGS. 6A/6B and FIG. 7, respectively. Recesses may be provided in each of the anchors 612 and 614 and the protrusion 618 for attachment of tissue in-growth promoting material such as Dacron fabric attached by suture-like material to cover the top, bottom and side surfaces. Otherwise, anchors 612 and 614 may be the same as anchors 112 and 114 described previously.

Protrusion 618 may include a center rotating member 642 coupled to cross member 644 by pivot connection 646. The rotating member 642 may be rotated 90 degrees relative to cross member 644 about pivot 646 as indicated by arrows 640. The rotating member 642 may be rotated as indicated by arrows 640 between a low profile delivery configuration wherein the rotating member 642 is generally aligned with the cross member 644, and a deployed configuration wherein the rotating member 642 is generally orthogonal to the cross member 644 as shown. The rotating member 642 may be rotationally biased to the deployed configuration and may be locked in the deployed configuration. A pair of protrusions 648 may be disposed at opposite ends of the cross member 644. The rotating member 642 in addition to the protrusions 648 may function as protrusions as described previously, while the gap therebetween may be used to avoid critical anatomical structures such as coronary vasculature.

Figure 5D:
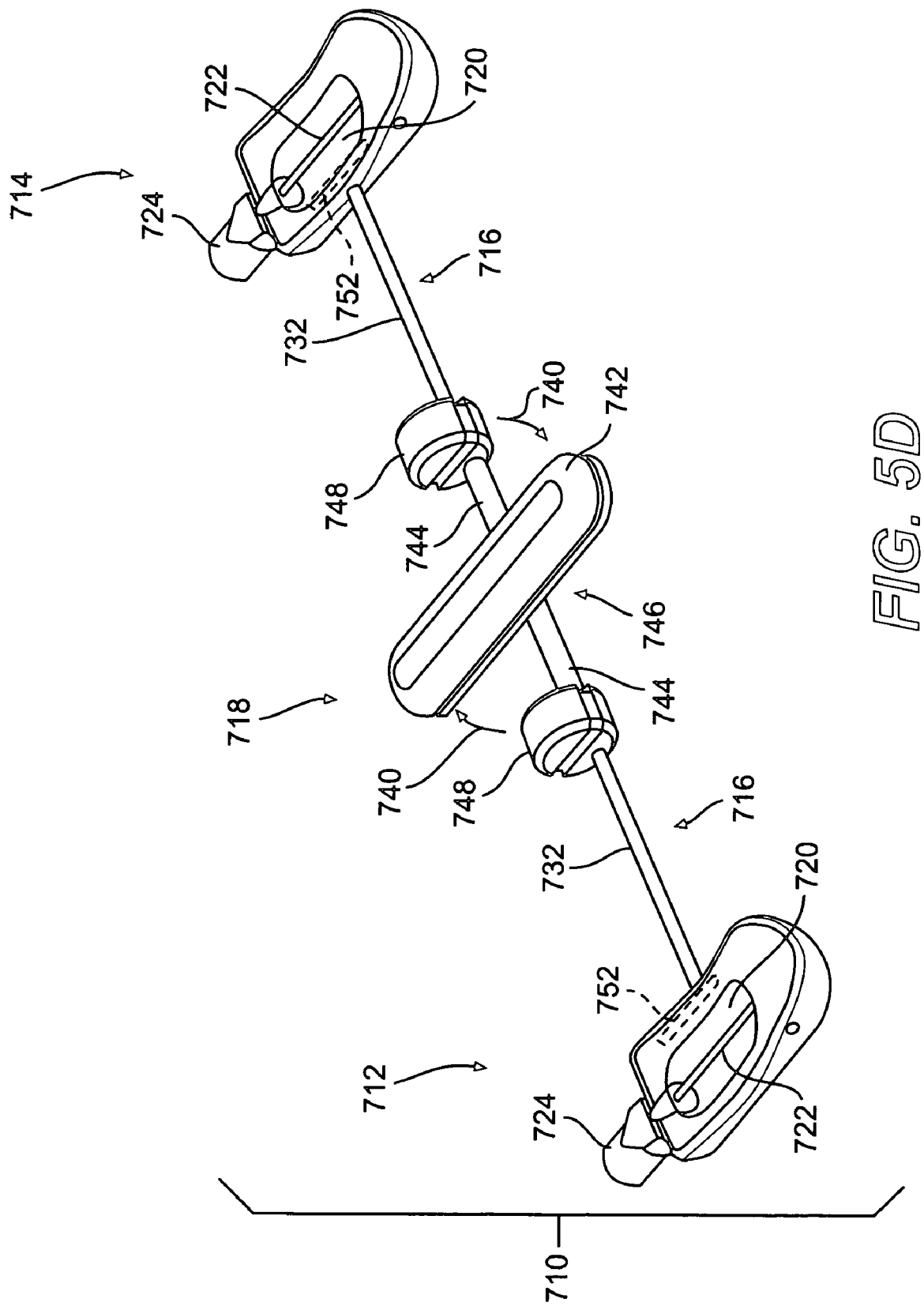
Figure 5E:
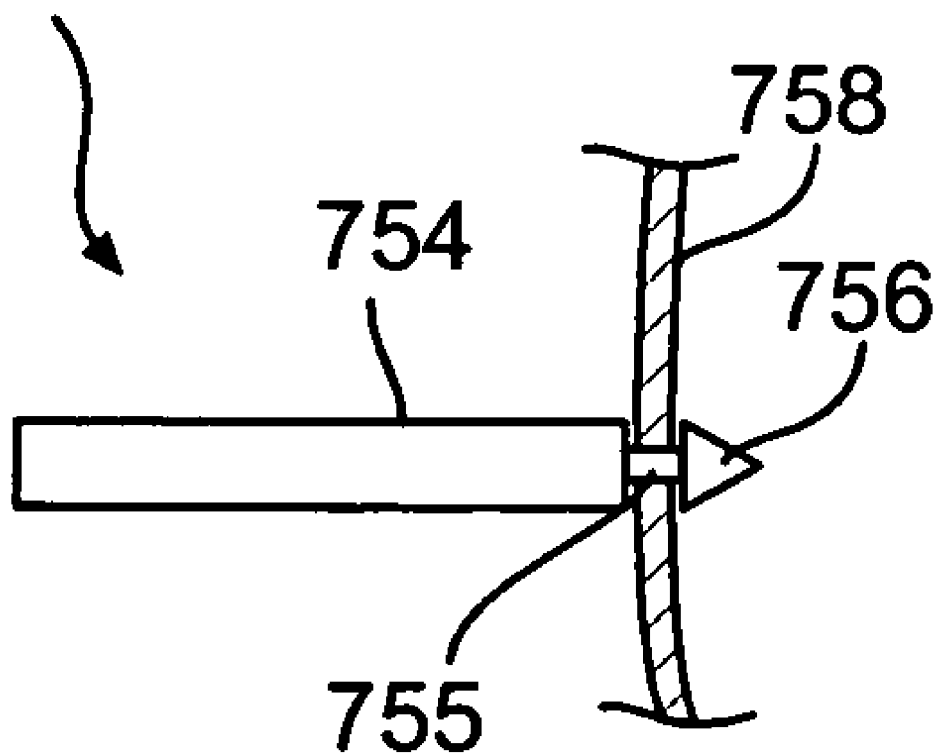
FIG. 5E is a schematic illustration of a cable locking mechanism for use in any of the implantable devices shown in FIGS. 5A-5D.

As seen in FIG. 5D, implantable device 710 includes a first anchor 712, a second anchor 714, a interconnecting member 716, and a protrusion 718. In this embodiment, the interconnecting member 716 includes cable 732 fixedly attached to and extending through protrusion 718, with both ends of the cable 732 adjustably connected to the anchors 712 and 714 by pins 752 to selectively lock and adjust the length of the interconnecting member 716. Anchors 712 and 714 include interior cavities 720 in fluid communication with a vacuum source to accommodate heart tissue for securement thereto by tissue piercing pins 722. A port 724 in communication with the interior of the cup 720 is provided for releasable connection to an anchor catheter 400 or 800 as shown and described with reference to FIGS. 6A/6B or FIG. 7, respectively. Recesses may be provided in each of the anchors 712 and 714 and the protrusion 718 for attachment of tissue in-growth promoting material such as Dacron fabric attached by suture-like material to cover the top, bottom (inside anchor) and side surfaces (away from heart surface). Otherwise, anchors 712 and 714 may be the substantially the same as anchors 112 and 114 described previously.

Protrusion 718 may include a center rotating member 742 coupled to cross member 744 by pivot connection 746. The rotating member 742 may be connected to the cross member 744 by an elastic ring and may be rotated 90 degrees relative to cross member 744 about pivot 746 as indicated by arrows 740. The rotating member 742 may be rotated as indicated by arrows 740 between a low profile delivery configuration wherein the rotating member 742 is generally aligned with the cross member 744, and a deployed configuration wherein the rotating member 742 is generally orthogonal to the cross member 744 as shown. The rotating member 742 may be rotationally biased to the deployed configuration and may be locked in the deployed configuration. A pair of protrusions 748 may be disposed at opposite ends of the cross member 744. The rotating member 742 in addition to the protrusions 748 may function as protrusions as described previously, while the gap therebetween may be used to avoid critical anatomical structures such as coronary vasculature.

As seen in FIG. 5E, an example of a lock mechanism is shown to secure tissue piercing pins 722 and/or cable piercing pins 752. The pins 722/752 may include a cylindrical shaft 754 and a sharpened tip 756 with a recess 755 therebetween. A braided multifilament material 758 such as Spectra™ is provided distal of the pins 722/752 in the anchor housing 712/714 to catch the recess 755 of the pins 722/752 when the tip 756 is advanced therethrough. This effectively locks the pins 722/752 in the advanced position to secure the interconnecting member 716 to the anchors 712 and 714 and/or to secure the anchors 712 and 714 to the heart tissue as will be described in more detail hereinafter.

Exemplary Embodiments of Delivery Devices

Figure 6A:
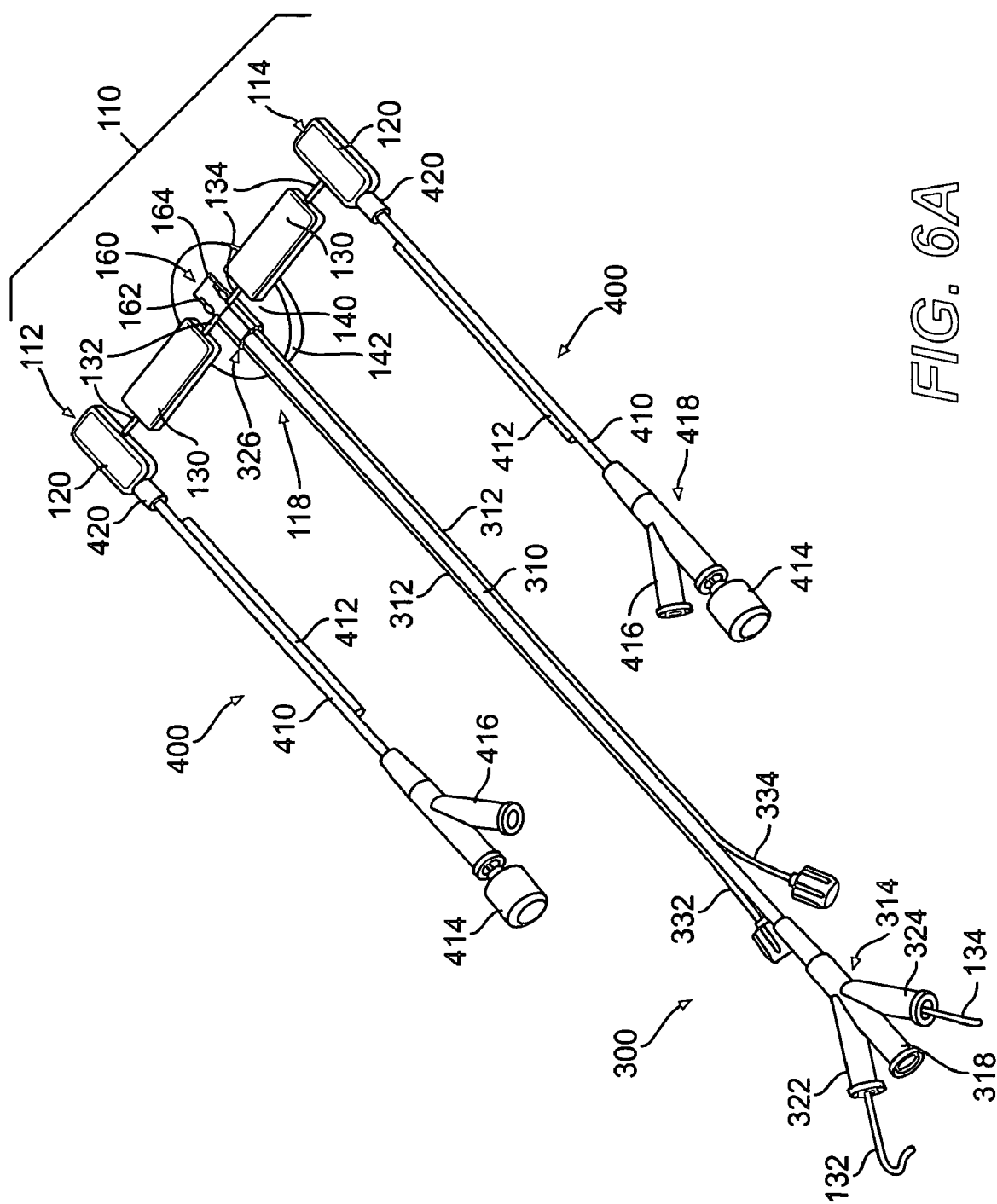
FIG. 6A is a perspective plan view of a delivery system for implanting the implantable devices shown in FIGS. 5A-5D.

With reference to FIG. 6A, an example of a delivery system for delivery and implanting device 110 is shown. The delivery system generally includes a delivery catheter 300 and two anchor catheters 400, all of which are releasably connected to the implantable device 110. The illustrated delivery system is particularly suitable for delivering implantable device 110, but may also be modified for delivery of implantable devices 210, 610 and 710. The delivery system may be configured in terms of size, length, flexibility, radiopacity, etc., to facilitate a transthoracic delivery approach such as the subxiphoid delivery approach described with reference to FIG. 11.

The delivery catheter 300 includes a tubular shaft 310 defining an inflation lumen and two cable lumens extending therethrough. A pair of push tubes 312 extend along side the tubular shaft 310 and slidably accommodate push rods 332 and 334. The distal ends of the tubular shaft 310 and push tubes 312 are coupled to the locking mechanism 160 by a release mechanism 326 such as a threaded, pinned or other releasable connection, such as the pin mechanism illustrated in FIG. 5E. The push rods 332 and 334 may be advanced or retracted to selectively actuate individual pins 162 and 164 respectively in the lock mechanism 160 such that the pins 162 and 164 pass through the cables 132 and 134, respectively, and thus lock the cables relative thereto. Reference may be made to published U.S. Patent Application No. 2003/0050529 to Vidlund et al., the disclosure of which is incorporated herein by reference, for an example of a similar locking mechanism.

The proximal end of the tubular shaft 310 is connected to a manifold including connectors 322 and 324 and inflation port 318. The inflation lumen of the tubular shaft 310 provides fluid communication between the interior of the balloon 142 and the inflation port 318 of the manifold 314 for connection to an inflation device (not shown) to facilitate inflation and deflation of the balloon 142. If no balloon 142 is used, the inflation lumen and associated parts may be eliminated. The cable lumens of the tubular shaft 310 accommodate the proximal portions of the cables 132 and 134 for connection to a sizing device 500 via connectors 322 and 324 as described with reference to FIG. 8, and for positioning the implant 110 relative to the anchors 112 and 114.

Figure 6B:
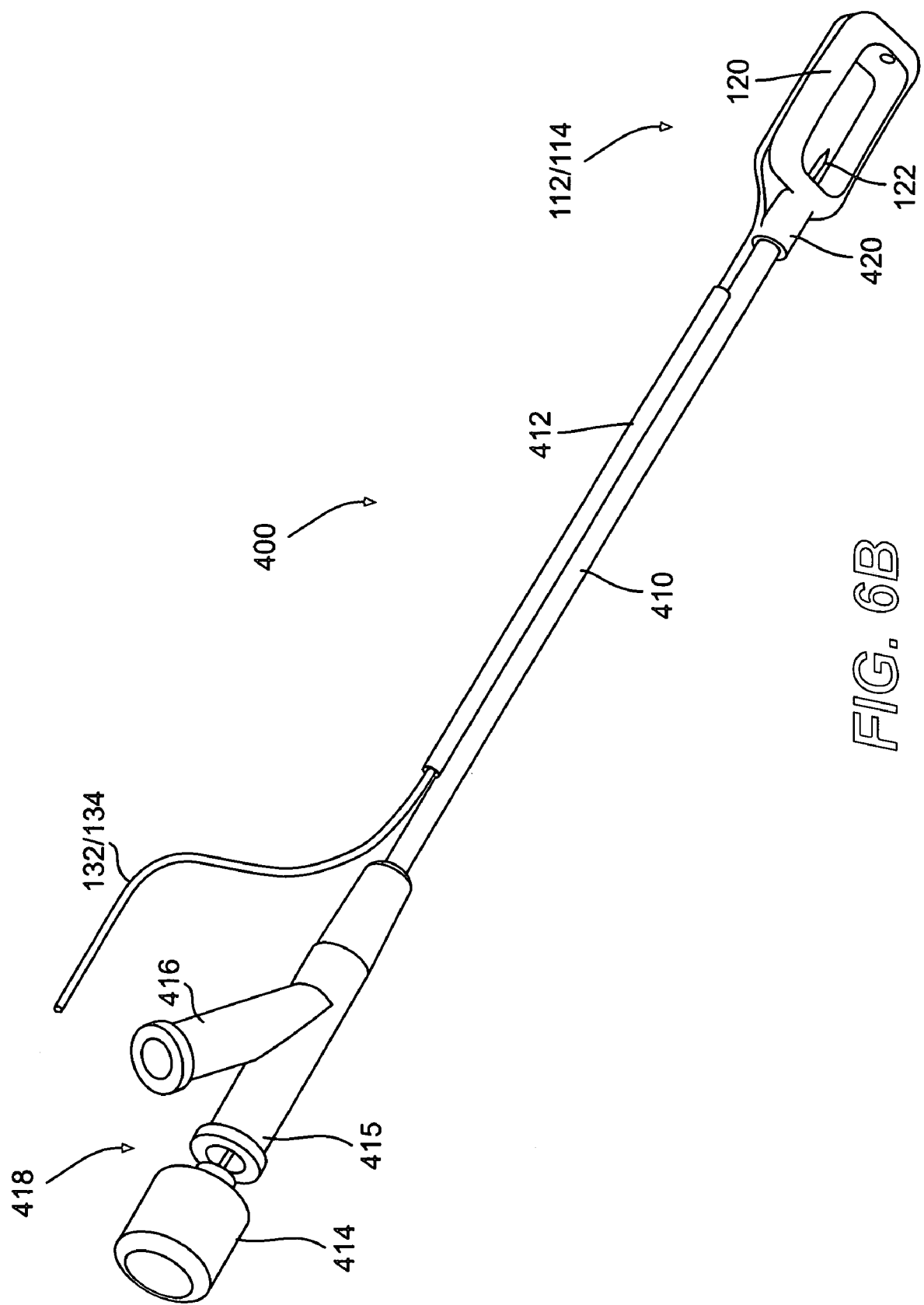
FIG. 6B is a perspective bottom view of an anchor catheter for use in the delivery system shown in FIG. 6A.

With additional reference to FIG. 6B, the anchor catheters 400 are essentially mirror constructions of each other, and include a tubular shaft 410. A slit guide tube 412 extends along side a portion of the tubular shaft 410 to guide the cable 132/134 before the delivery catheter 300 is advanced as will be discussed in more detail hereinafter. A proximal end of the tubular shaft 410 is connected to a manifold 418 including a vacuum port 416 and a gasketed port 415 containing a push rod 414. A distal end of the tubular shaft 410 is releasably connected to the anchor 112/114 by a release mechanism 420 that may comprise a threaded, pinned or other releasable connection, for example. The tubular shaft 410 includes a vacuum lumen (not visible) extending therethrough to provide a fluid path from the interior of the cup 120 to the vacuum port 416 to facilitate connection to a vacuum source. The push rod 414 is disposed in the vacuum lumen of the catheter shaft 410 and may be slid therethrough to selectively advance or retract the piercing pin 122 in the cup 120.

Figure 7:
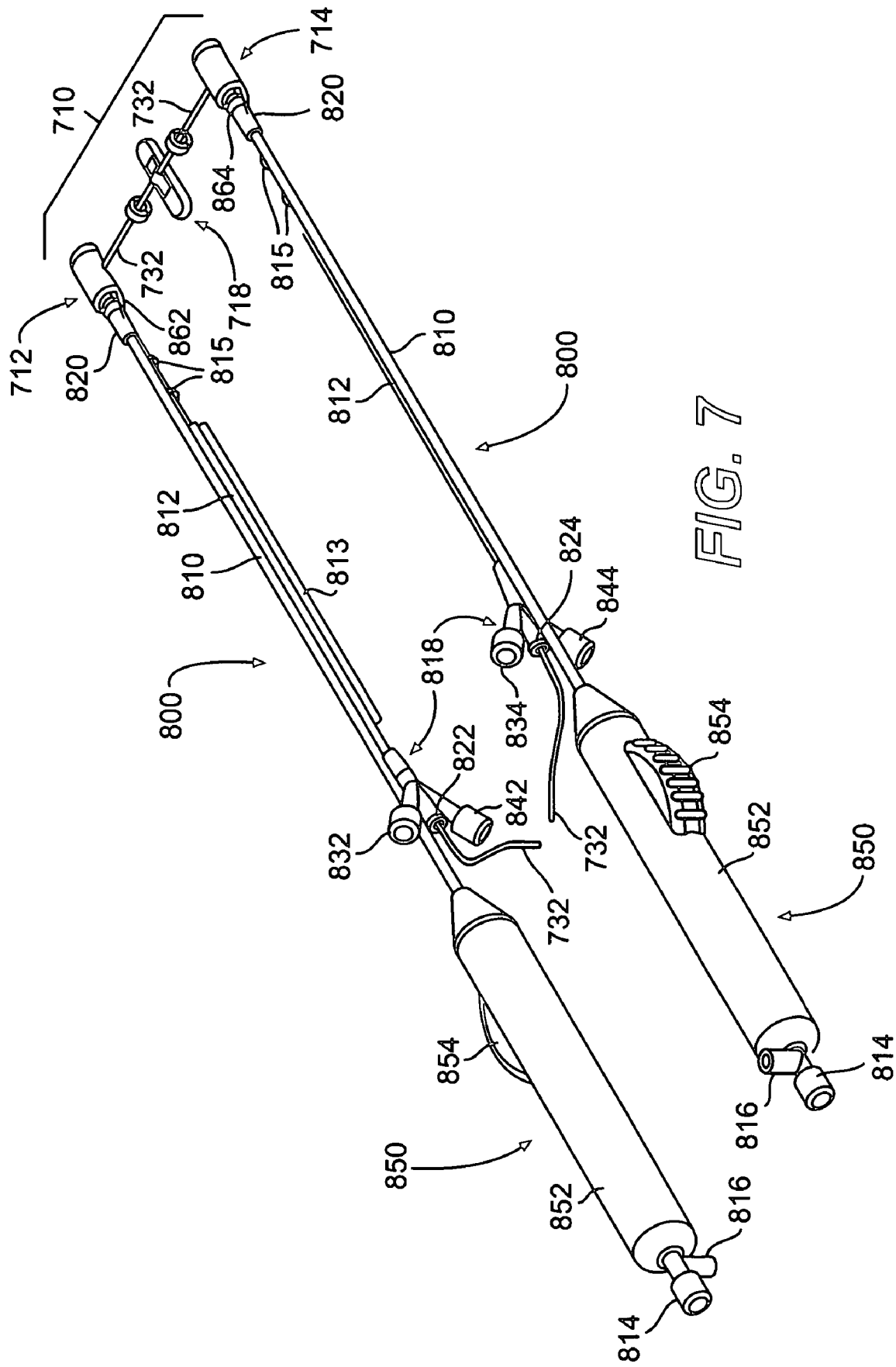
FIG. 7 is a perspective plan view of an alternative delivery system for implanting the implantable devices shown in FIGS. 5A-5D.

With reference to FIG. 7, an example of a delivery system for delivery and implanting device 710 is shown. The delivery system generally includes a two anchor catheters 800, both of which are releasably connected to the implantable device 710. The illustrated delivery system is particularly suitable for delivering implantable devices 210, 610 and 710, but may also be modified for delivery of implantable device 110. The delivery system may be configured in terms of size, length, flexibility, radiopacity, etc., to facilitate a transthoracic delivery approach such as the subxiphoid delivery approach described with reference to FIG. 11.

The anchor catheters 800 are essentially mirror constructions of each other (with the exception of split tube 813), and include a tubular shaft 810 comprising a directional catheter construction connected to a handle 850. The directional catheter shaft 810 and associated handle 850 are available from Medamicus, Inc. of Plymouth, Minn. Handle 850 generally includes a grip portion 852 and a thumb knob 854 which actuates control wires in the directional catheter shaft 810 to permit selective bi-directional lateral deflection of the distal end thereof. The directional catheter shaft 810 and associated handle 850 accommodate a push rod (not visible) extending therethrough for actuation of the tissue piercing pin 722. The push rod for the tissue piercing pin 722 may comprise a stainless steel mandrel, for example, with a distal end abutting the proximal end of the tissue piercing pin 722, and a proximal end connected to a knob 814. The directional catheter shaft 810 and associated handle 850 also accommodate a vacuum lumen (not visible) extending therethrough to define a fluid path to the interior 720 of the anchor 712/714, such that a vacuum source (not shown) may be connected to vacuum port 816 on the handle 850 to provide suction at the anchor 712/714 to facilitate stabilization and securement to the outside of the heart wall.

Each of the anchor catheters 800 also includes a side tube 812 coextending with the directional catheter shaft 810. Side tube 812 accommodates the interconnecting member 732, a push rod (not visible) for actuation of the interconnecting member piercing pin 752, and a pull wire (not visible) for release of the anchor 712/714 as described in more detail below. The interconnecting member 732 extends through the side tube 812 from a proximal port 822/824 through the anchor 712/714 to the protrusion 718. To accommodate the interconnecting member 732 during initial delivery of the implant 710, a slotted side tube 813 may be provided on one of the catheters 800.

The push rod for the interconnecting member piercing pin 752 may comprise a stainless steel mandrel, for example, with a distal end abutting the proximal end of the interconnecting member piercing pin 752, and a proximal end connected to knob 832/834. A pair of guide loops 815 may be provided distal of the side tube to guide the interconnecting member 732, and a guide tube 862/864 may be provided distal of the side tube 812 to guide the push rod for the interconnecting member piercing pin 752.

The distal end of the directional catheter shaft 810 is connected to anchor 712/714 by a releasable connection 820, which may comprise a threaded type connection or a cotter pin type connection, for example. In the illustrated embodiment, the releasable connection 820 comprises a cotter pin type connection, with the pull wire (not visible) proximally connected to pull knob 842/844, and distally extending through aligned holes (not visible) in the anchor 712/714 and in the fitting on the distal end of the directional catheter shaft 810. By pulling proximally on pull knob 842/844, the anchor 712/714 may be released from the distal end of the directional catheter shaft 810.

Figure 8:
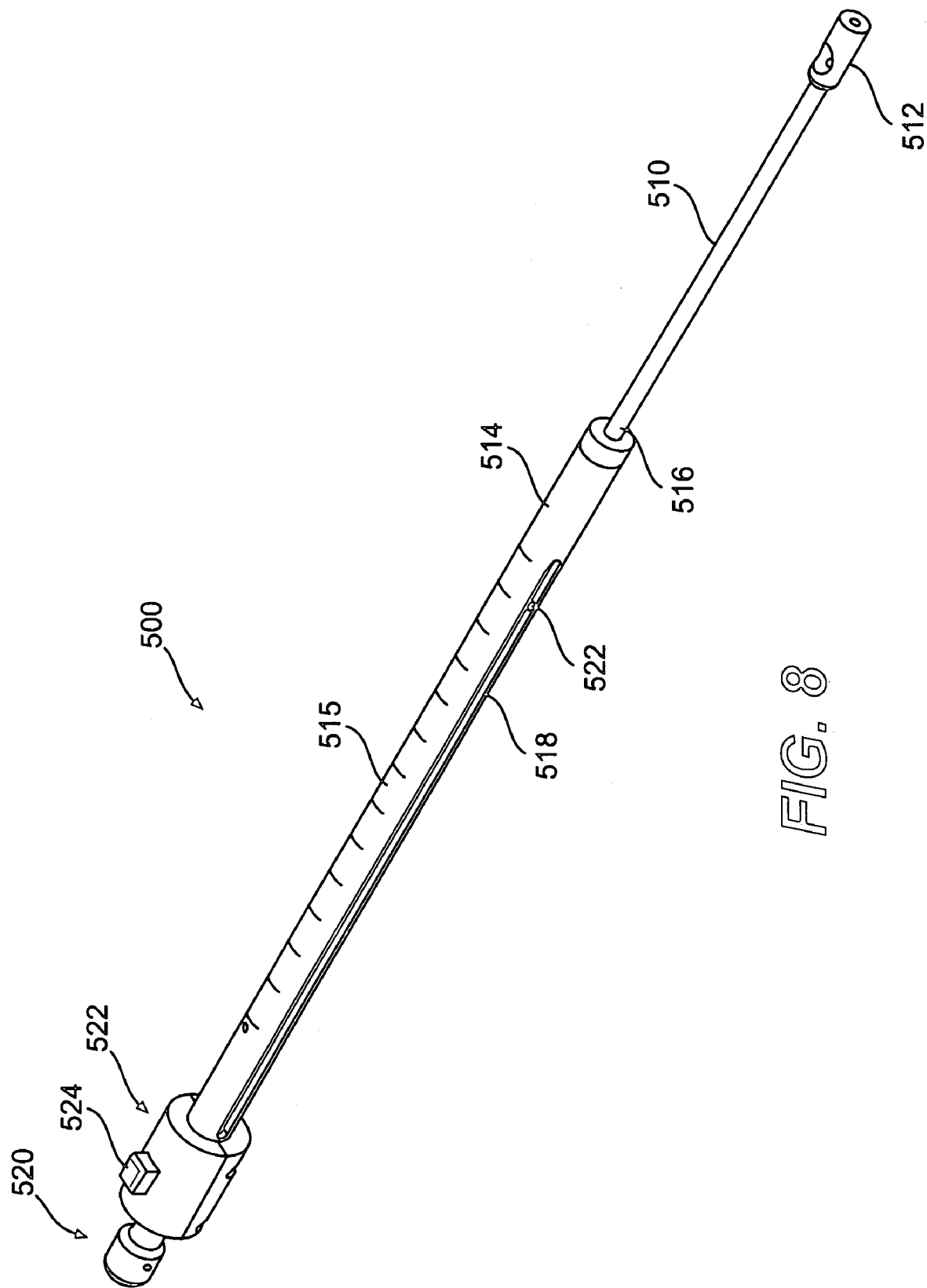
FIG. 8 is a perspective view of a sizing device for use in adjusting the implantable devices shown in FIGS. 5A-5D.

With reference to FIG. 8, a sizing device 500 is shown for adjusting the tension of interconnecting member 116, 216, 616, or 716 and in particular cable members 132/134, 232, 632 or 732. Sizing device 500 includes an elongate interconnecting member receiving tube 510 having a distal end including an engagement member 512 and a proximal end 516 connected to a preferably clear measuring tube 514 having a measuring scale 515 marked thereon. An inner tube 518 is disposed in the measuring tube 514 and is connected to a proximal end of the cable member to be tensioned. A lock mechanism 522 and release button 524 (biased in locked position) are connected to the proximal end of the measuring tube 514 to selectively lock the inner tube 518 relative to the measuring tube. A pin 522 protruding from inner tube 518 extends through a slot in measuring tube 514 to prevent relative rotation. An indicator (not visible) on the inner tube 518 adjacent the pin 522 is visible through transparent measuring tube 514 to facilitate linear measurement relative to scale 515.

To connect the cable to the inner rod or tube 518, the cable 132/134, 232, 632 or 732 is threaded through receiving tube 510, through measuring tube 514, through the inner tube 518, and placed in a retaining mechanism 520 disposed on the inner tube 518. Engagement member 512 may be connected to one of the connectors 322/324 or 822/824 on the delivery catheter, or directly to the lock mechanism 160 of device 110 or lock mechanism of device 210. With this arrangement, the inner tube 518 may be pulled proximally relative to the measuring tube 514 to apply tension to the cable and thus selectively adjust the tightness or degree of cinching of the implantable device 110/210/610/710, and/or selectively adjust the position of the protrusion relative to the anchor ends.

Exemplary Embodiments of Access Devices

Figure 9:
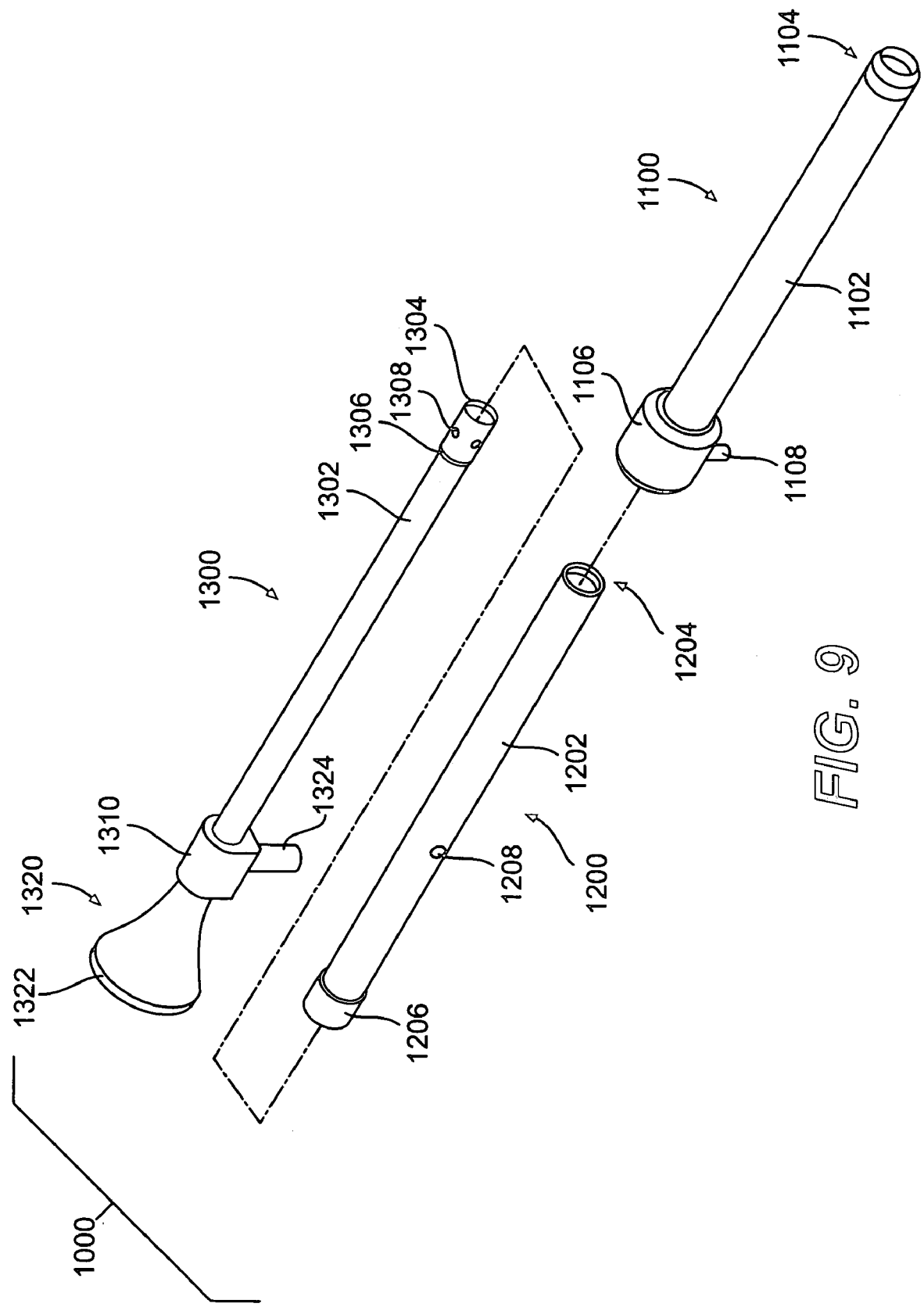
FIG. 9 is a perspective exploded view of an access system to facilitate pericardial access of the delivery systems.

With reference to FIG. 9, an exemplary embodiment of an access device 1000 is shown. Access device 1000 provides for less invasive surgical access from a point outside the patient's body, through a transthoracic port to the pericardial space around the patient's heart, as will be described in more detail with reference to FIG. 11. A variety of pericardial access devices may be used to delivery the implantable device 10, and thus access device 1000 is shown by way of example not limitation. In this exemplary embodiment, access device 1000 includes an outer tube 1100, a securement tube 1200, and a cutter tube 1300. The securement tube 1200 is slidably and coaxially disposed in outer tube 1100, and similarly, the cutter tube 1300 is slidably and coaxially disposed in the securement tube 1200.

Outer tube 1100 may comprise a rigid tubular shaft 1102 formed of stainless steel, for example, having a lumen extending therethrough. A cap 1104 having an interior recess (not visible) may be connected to the distal end of the shaft 1102. A handle 1106 may be connected to a proximal end of the tubular shaft 1102 to facilitate manual manipulation. A vacuum port 1108 may be incorporated into the handle 1106 to facilitate connection to a vacuum source (not shown) for establishing a vacuum in the lumen extending through the tubular shaft 1102.

The securement tube 1200 may comprise a rigid tubular shaft 1202 formed of stainless steel, for example, having a lumen extending therethrough. An annular array of pericardium piercing pins 1204 may be disposed at the distal end of the tubular shaft 1202, and are sized to fit in the recess inside cap 1104 at the distal end of the outer tube 1100 as will be discussed in more detail with reference to FIG. 10. A handle 1206 may be disposed at the proximal end of the tubular shaft 1202 to facilitate manual manipulation and to act as a stop to prevent the securement tube 1200 from advancing fully into outer tube 1100. A vacuum hole 1208 may be provided through the side of the tubular shaft 1202 to provide a fluid path from the interior of the outer tube 1100 to the interior of the securement tube 1200, thus permitting a vacuum to be established inside the tubular shaft 1202 of the securement tube 1200 by application of a vacuum to vacuum port 1108.

The cutter tube 1300 may comprise a rigid tubular shaft 1302 formed of stainless steel, for example, having a lumen extending therethrough. An annular cutting edge 1304 may be disposed at the distal end of the tubular shaft 1302. An annular ring 1306 may be disposed adjacent the distal end of the tubular shaft 1302 to provide a slidable fluid seal with the inside surface of the tubular shaft 1202 of the securement tube 1200. A series of vacuum holes 1308 may be provided through the side of the tubular shaft 1302 distal of the annular ring 1306 to provide a fluid path from the interior of the securement tube 1200 to the interior of the cutter tube 1300, thus permitting a vacuum to be established inside the tubular shaft 1302 of the cutter tube 1300 by application of a vacuum to vacuum port 1108. A handle 1310 may be disposed at the proximal end of the tubular shaft 1302 to facilitate manual manipulation and to act as a stop to prevent the cutter tube 1300 from advancing fully into securement tube 1200. A visualization device 1320 such as a camera or eye piece 1322 and light source 1324 may be connected to the proximal end of the tubular shaft 1302 to permit direct visualization down the lumen of the cutter tube 1300. Alternatively, an intracardiac echo device may be inserted therethrough, using vacuum for stability, to permit visualization and guidance on the epicardial surface.

Figure 10:
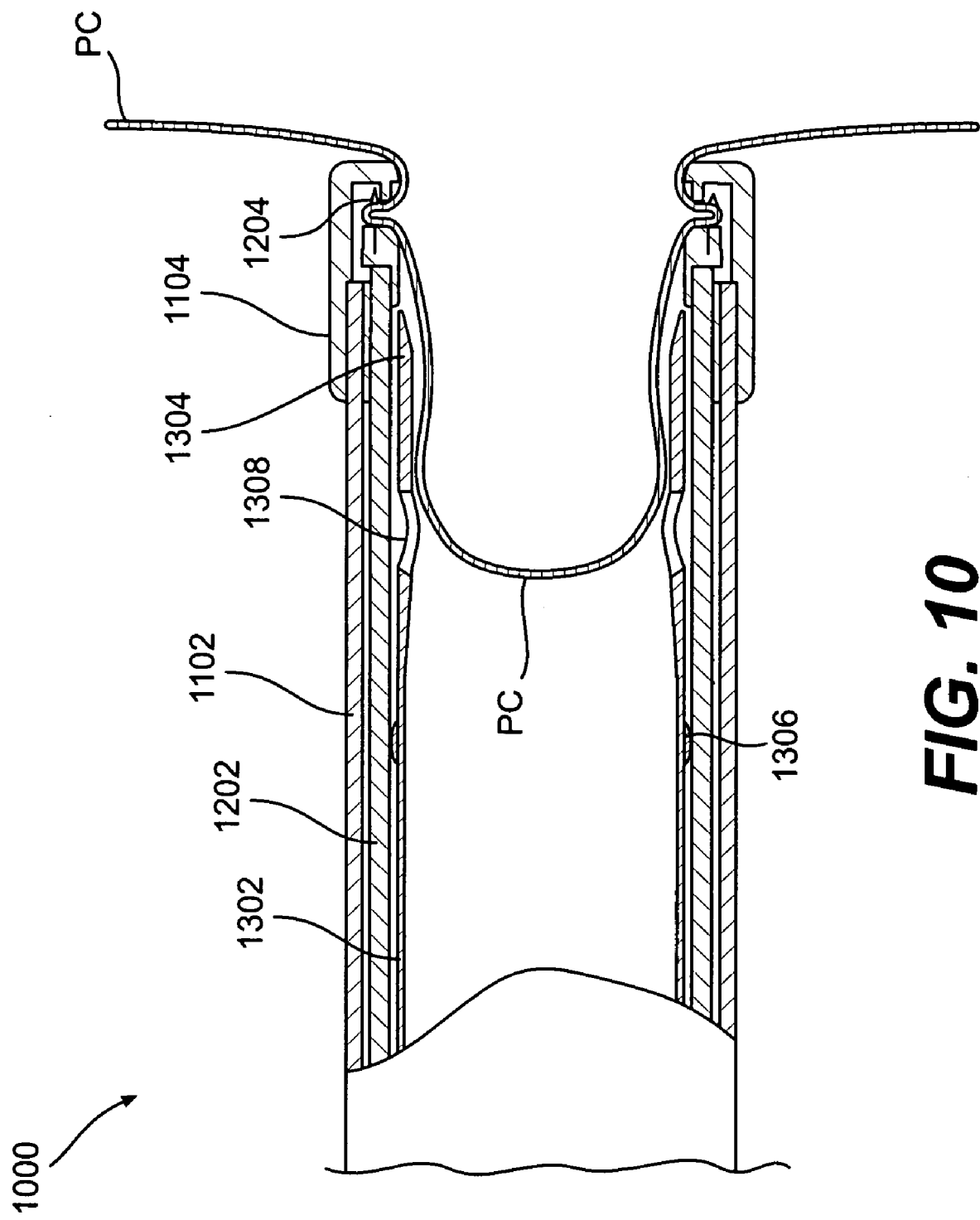
FIG. 10 is a partially sectioned side view of a distal portion of the access device shown in FIG. 9, illustrating engagement with the pericardial sac.

With reference to FIGS. 9 and 10, the operation of the distal portion of the access device 1000 may be appreciated. The cutter tube 1300 and the securement tube 1200 may be disposed in the outer tube 1100 with the distal ends thereof slightly retracted. The outer tube 1100 may be inserted through a transthoracic port until the distal cap 1104 engages the pericardium (PC) surrounding the heart. Vacuum is applied to port 1108 thus drawing the PC into the lumen of the outer tube 1100, the securement tube 1200, and the cutter tube 1300 to form inward protrusion. The vacuum also draws the PC into the interior recess of the cap 1104 to form an annular fold. The securement tube 1200 may then be advanced distally until the array of pins 1204 passes through the annular fold in the PC, thus mechanically securing and sealing the PC to the access device 1000. The cutter tube 1300 may then be advanced distally until the annular cutting edge 1304 cuts the inward protrusion of the PC, leaving the annular fold of the PC secured to the access device 1000. With the annular fold of the PC mechanically and sealingly connected to the distal end of the access device 1000, and with the outside diameter of the access device 1000 sized to form a seal in the transthoracic port, a sealed access path is established to the pericardial space that is isolated from the pleural space.

Exemplary Embodiments of Access and Delivery Methods

Figure 11:
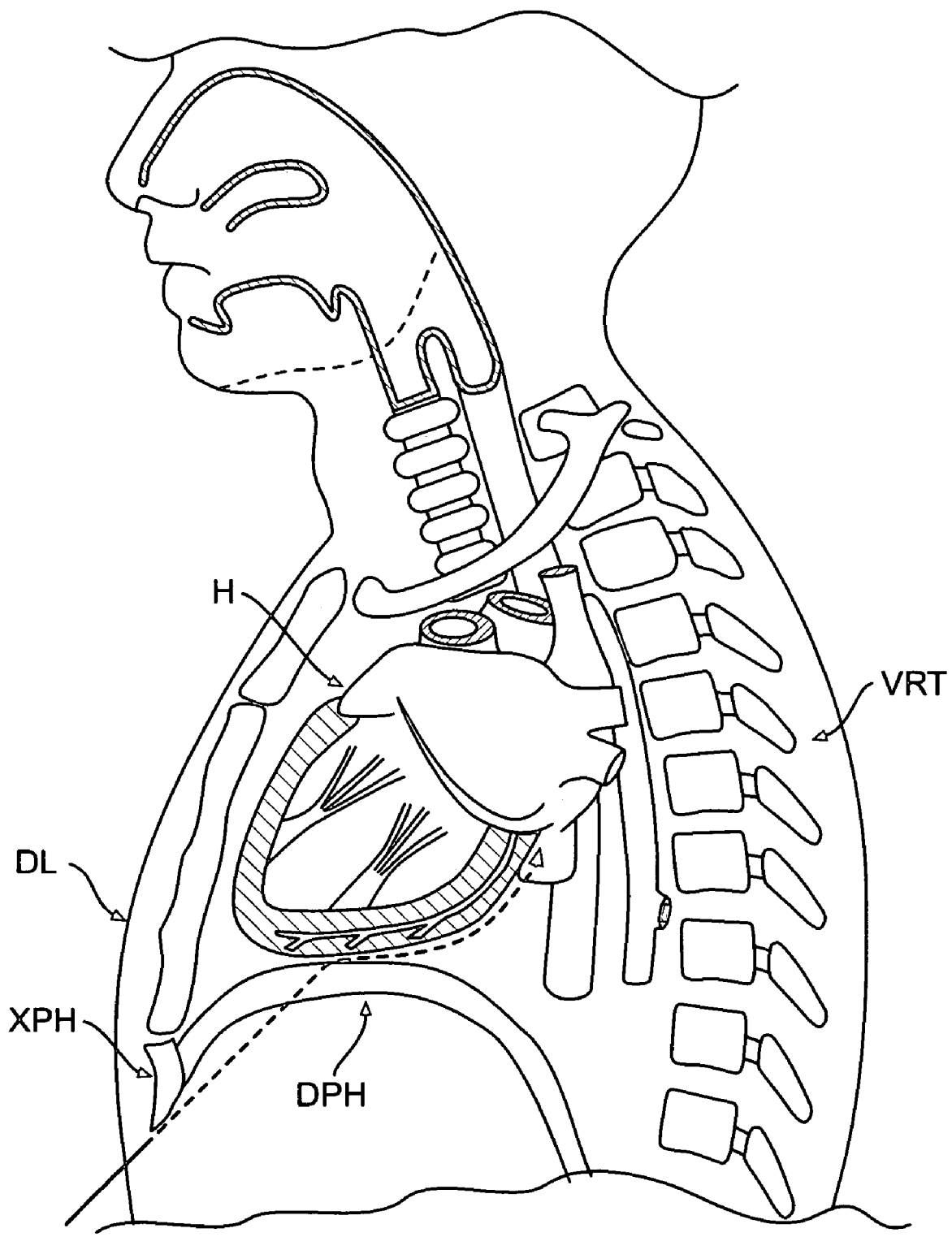
FIG. 11 is an illustration schematically showing a pericardial access approach for delivery of the implantable devices.

In FIG. 11, a transthoracic anterior approach is shown as a dashed line with a distal arrow. This anterior approach may comprise a subxiphoid approach to establish access to the pericardial space, similar to the technique described by Kaplan et al. in U.S. Pat. No. 6,423,051 the entire disclosure of which is incorporated herein by reference. An alternative lateral or posterior approach may utilize similar tools and techniques to access the pericardial space from the side or back between the ribs (intercostal space), similar to the techniques described by Johnson in U.S. Pat. No. 5,306,234 the entire disclosure of which is incorporated herein by reference.

Generally speaking, once pericardial access is established with an access system as described with reference to FIGS. 9 and 10, a delivery system as described with reference to FIGS. 6 and 7 may be used to advance and manipulate the device 10 to the desired deployment position in the pericardial space adjacent the mitral valve MV or a specific part thereof. Assessment of the position and function of the device 10 relative to internal mitral valve MV structures such as leaflets AL/PL, papillary muscles PM, and regurgitant jet may be performed with ultrasonic imaging such as trans-esophageal, intracardiac or epicardial echocardiography, or x-ray fluoroscopy. These techniques may also be used monitor the adjustment of the size and/or tension of the device 10 with an adjustment device as described with reference to FIG. 8 until the desired acute effect is established. Once in the desired position, the device 10 may be detached or otherwise disengaged from the distal end of the delivery system, which is subsequently removed.

The following detailed example of a delivery method using the delivery system and implant illustrated in FIG. 7 is described by way of example, not limitation, and may be applied to other delivery systems and implants described herein. This method may be broken down into six general steps: (1) establish pericardial access; (2) deliver the first anchor (e.g., near the PDA); (3) deliver the protrusion; (4) deliver the second anchor (e.g., near the LAD); (5) adjust the implant to achieve the desired effect on MV function; and (6) remove the delivery system leaving the implant in place on the outside of the heart.

To establish pericardial access, a needle may be inserted into the chest cavity below the xiphoid as generally shown in FIG. 11. A guide wire (e.g., 0.035" diameter) may then be inserted into the needle and advanced toward the cardiac space. The needle may then be removed leaving the guide wire in place, and one or more dilators may then be advanced over the guide wire to dilate the percutaneous path. The dilator(s) may then be removed, and the access device illustrated in FIG. 9 may be advanced over the wire adjacent the pericardium. Fluoroscopic visualization (e.g., AP and lateral views) may be used to confirm the desired pericardial access site.

Using the access device illustrated in FIG. 9, vacuum may be applied to cause the pericardium to be sucked into the distal end thereof, and the tissue piercing pins may be actuated to mechanically secure the pericardium to the access device. The cutter tube may then be advanced to cut and remove a portion of the pericardium in the distal end of the access device, thus establishing a path from the exterior of the body to the pericardial space around the heart.

Initially, the interconnecting member may be loaded into the first anchor and anchor catheter with one side of the interconnecting member extending through the side tube and the other side of the interconnecting member extending through the slotted side tube. Before delivering the anchor, angiographic visualization of the left and/or right coronary arteries may be performed to map the locations of the critical arteries. To deliver the first anchor near the PDA as shown in FIG. 4, for example, the anchor catheter may be manipulated through the access device until the anchor is adjacent the PDA near the last obtuse marginal (OM3), using fluoroscopic visualization to aid navigation. After ascertaining that the first anchor is not positioned over any coronary arteries, vacuum may be applied to the first anchor to temporarily stabilize the anchor on the outside of the heart wall and to pull tissue into the interior of the anchor. The tissue piercing pins may then be actuated to secure the first anchor to the heart wall.

The protrusion may then be advanced along the first anchor catheter by removing one end of the interconnecting member from the slotted tube on the anchor catheter, inserting it through the protrusion and fixing the protrusion midway on the interconnecting member. A delivery tube may be placed about the protrusion to retain it in the delivery configuration, and the delivery tube with the protrusion therein may then be inserted through the access device. By pulling on the opposite end of the interconnecting member and by manipulating the delivery tube, the protrusion may be advanced until it is adjacent the first anchor.

Before delivering the second anchor near the LAD as shown in FIG. 4, the interconnecting member may be inserted into the second anchor and through the side tube of the second anchor catheter. The second anchor may then be slid over the interconnecting member using the anchor catheter, passing through the access device and into the pericardial space. With the aid of fluoroscopic guidance, the second anchor may be positioned next to the junction of the LAD and CFX as seen in FIG. 4, for example. After ascertaining that the second anchor is not positioned over any coronary arteries, vacuum may be applied to the second anchor to temporarily stabilize the anchor on the outside of the heart wall and to pull tissue into the interior of the anchor. The tissue piercing pins may then be actuated to secure the second anchor to the heart wall.

With the first and second anchors secured to the outside of the heart wall, and the protrusion extending therebetween, the interconnecting member may be tightened or cinched using the device illustrated in FIG. 8, for example. MV function may be simultaneously observed using TEE or ICE, and the degree of cinching of the interconnecting member and/or the position of the protrusion may be adjusted to obtain the desired reduction in MV regurgitation (MVR).

With the aid of fluoroscopy, correct anchor positioning may be verified and adequate blood flow may be confirmed in the left coronary arteries. After confirming correct positioning and adequate reduction in MVR, the interconnecting members may be secured by actuating interconnecting member piercing pins with the associated push rods, and the directional catheter shaft may be disconnected from the anchors by actuating the releasable connection with the associated pull wires.

The delivery system may then be removed, and the interconnecting members may be trimmed adjacent the anchors with a cutting device such as an elongate cautery tool. The access device may be removed and the sub-xiphoid access site may be closed using sutures.

From the foregoing, it will be apparent to those skilled in the art that the present invention provides, in exemplary non-limiting embodiments, devices and methods for improving the function of a valve (e.g., mitral valve) by positioning an implantable device outside and adjacent the heart wall such that the device applies an inward force against the heart wall or otherwise deforms the heart wall thus acting on the valve to improve leaflet coaptation. Further, those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method for improving heart valve function, the method comprising:
   providing a device comprising a first anchor configured to be secured to heart tissue, a second anchor configured to be secured to heart tissue, and an interconnecting member connecting the first anchor and the second anchor;
   delivering the device to a heart via a transthoracic sub-xiphoid approach;
   positioning at least a portion of the interconnecting member in contact with an external surface of a heart wall proximate a valve such that the device exerts an inward force on the heart wall sufficient to alter the valve function; and
   securing the first anchor and the second anchor to an epicardial layer of the heart,
   wherein the interconnecting member is configured to be selectively adjustable so as to alter a tension of the interconnecting member between the first anchor and the second anchor.

2. The method of claim 1, wherein the inward force is sufficient to draw leaflets of the valve together.

3. The method of claim 2, wherein the valve leaflets define a line of coaptation and positioning the portion of the interconnecting member includes positioning the portion such that the inward force is exerted substantially orthogonal to the line of coaptation.

4. The method of claim 1, wherein the valve is a mitral valve.

5. The method of claim 1, wherein the inward force is exerted on an annulus of the valve.

6. The method of claim 1, wherein the inward force is sufficient to reposition papillary muscles of the valve.

7. The method of claim 1, further comprising positioning the device outside the epicardium of the heart.

8. The method of claim 1, further comprising selectively adjusting the tension of the interconnecting member.

9. The method of claim 1, further comprising adjusting a relative position of the first and second anchors so as to adjust the tension in the interconnecting member.

10. The method of claim 9, further comprising selectively locking the interconnecting member to at least one of the first anchor and the second anchor after adjusting the relative position.

11. The method of claim 10, wherein the selectively locking includes penetrating the interconnecting member with a pin.

12. The method of claim 1, wherein the securing includes securing the first anchor and the second anchor to the epicardial layer while the anchors remain free from a pericardial layer of the heart.

13. The method of claim 1, further comprising securing at least one of the first anchor and the second anchor to a pericardial layer of the heart.

14. The method of claim 1, further comprising delivering the device to the heart via a delivery catheter.

15. The method of claim 1, further comprising securing the first and second anchors to the heart tissue via tissue penetrating members.

16. The method of claim 15, further comprising remotely actuating the tissue penetrating members.

17. The method of claim 1, further comprising exerting the inward force on the heart wall throughout a cardiac cycle.

18. The method of claim 1, wherein providing the device includes providing a device comprising at least one protrusion connected to the interconnecting member and disposed between the first anchor and the second anchor.

19. The method of claim 1, wherein the securing includes securing the first and second anchors directly to the epicardial layer of the heart.

20. A method for improving heart valve function, the method comprising:
 providing a device comprising a first anchor configured to be secured to heart tissue, a second anchor configured to be secured to heart tissue, and an interconnecting member connecting the first anchor and the second anchor;
 delivering the device via a transthoracic subxiphoid approach;
 positioning the device outside the epicardium of the heart; and positioning at least a portion of the interconnecting member in contact with an external surface of a heart wall proximate a valve such that the device exerts an inward force on the heart wall sufficient to alter the valve function,
 wherein the interconnecting member is configured to be selectively adjustable so as to alter a tension of the interconnecting member between the first anchor and the second anchor.

21. A method for improving heart valve function, the method comprising:
 providing a device comprising a first anchor configured to be secured to heart tissue, a second anchor configured to be secured to heart tissue, and an interconnecting member connecting the first anchor and the second anchor, wherein the interconnecting member is configured to be selectively adjustable so as to alter a tension of the interconnecting member between the first anchor and the second anchor;
 delivering the device via a transthoracic subxiphoid approach;
 positioning at least a portion of the interconnecting member in contact with an external surface of a heart wall proximate a valve such that the device exerts an inward force on the heart wall sufficient to alter the valve function;
 adjusting a relative position of the first and second anchors so as to adjust the tension in the interconnecting member; and
 selectively locking the interconnecting member to at least one of the first anchor and the second anchor after adjusting the relative position,
 wherein selectively locking the interconnecting member includes penetrating the interconnecting member with a pin.

22. A method for improving heart valve function, the method comprising:
 providing a device comprising a first anchor configured to be secured to heart tissue, a second anchor configured to be secured to heart tissue, and an interconnecting member connecting the first anchor and the second anchor, wherein the interconnecting member is configured to be selectively adjustable so as to alter a tension of the interconnecting member between the first anchor and the second anchor;
 delivering the device via a transthoracic subxiphoid approach; and
 positioning at least a portion of the interconnecting member in contact with an external surface of a heart wall proximate a valve such that the device exerts an inward force on the heart wall sufficient to alter the valve function.

* * * * *